United States Patent
Callister et al.

(10) Patent No.: US 8,435,278 B2
(45) Date of Patent: *May 7, 2013

(54) SYSTEM AND METHOD FOR DETERMINING AND CONTROLLING CORE BODY TEMPERATUE

(75) Inventors: Jeffrey Callister, Deep Haven, MN (US); Paul M. Stull, Bodega Bay, CA (US); Andrew E. Wu, Foster City, CA (US); David J. Scott, Redwood City, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/356,538

(22) Filed: Jan. 23, 2012

(65) Prior Publication Data

US 2012/0191166 A1    Jul. 26, 2012

Related U.S. Application Data

(63) Continuation of application No. 12/710,317, filed on Feb. 22, 2010, now Pat. No. 8,100,957, which is a continuation of application No. 10/525,625, filed as application No. PCT/US03/28683 on Sep. 12, 2003, now Pat. No. 7,666,215.

(60) Provisional application No. 60/410,096, filed on Sep. 12, 2002.

(51) Int. Cl.
*A61F 7/12*    (2006.01)

(52) U.S. Cl.
USPC .......................... 607/105; 607/104; 607/106

(58) Field of Classification Search .......... 607/104–106, 607/113
See application file for complete search history.

(56) References Cited

U.S. PATENT DOCUMENTS

| 3,425,419 | A | * | 2/1969 | Actis ............................. 607/106 |
| 3,504,674 | A | * | 4/1970 | Negrin Juan et al. ......... 607/105 |
| 3,744,555 | A | | 7/1973 | Fletcher et al. |
| 5,438,721 | A | * | 8/1995 | Pahno et al. ...................... 5/604 |
| 5,536,242 | A | * | 7/1996 | Willard et al. .................. 604/30 |
| 5,588,167 | A | * | 12/1996 | Pahno et al. ...................... 5/606 |
| 5,862,675 | A | | 1/1999 | Scaringe et al. |
| 6,063,079 | A | * | 5/2000 | Hovda et al. .................... 606/41 |

(Continued)

FOREIGN PATENT DOCUMENTS

| WO | 0010494 A1 | 3/2000 |
| WO | 00/42932 A1 | 7/2000 |
| WO | 02/07793 A2 | 1/2002 |
| WO | 02/11638 A1 | 2/2002 |

*Primary Examiner* — Linda Dvorak
*Assistant Examiner* — Kaitlyn Smith
(74) *Attorney, Agent, or Firm* — John J. Fitzgerald; Fulwider Patton LLP

(57) ABSTRACT

Systems and methods for accurate temperature modification of a patient, or selected regions thereof, including inducing hypothermia. The temperature modification is accomplished using an in-dwelling heat exchange catheter within which a fluid heat exchange medium circulates. A heat exchange cassette attached to the circulatory flow lines of the catheter, the heat exchange cassette being sized to engage a cavity within a control unit. A temperature measurement scheme for obtaining body core temperature is provided, including methods of obtaining and analyzing temperature data to provide feedback to the control unit for use in controlling the heating and cooling of the heat exchange medium so as to heat or cool a patient to a desired target temperature.

9 Claims, 12 Drawing Sheets

U.S. PATENT DOCUMENTS

| | | | |
|---|---|---|---|
| 6,139,571 A * | 10/2000 | Fuller et al. | 607/105 |
| 6,146,411 A | 11/2000 | Noda et al. | |
| 6,261,312 B1 | 7/2001 | Dobak, III et al. | |
| 6,497,721 B2 | 12/2002 | Ginsburg et al. | |
| 6,620,187 B2 * | 9/2003 | Carson et al. | 607/104 |
| 6,620,188 B1 * | 9/2003 | Ginsburg et al. | 607/106 |
| 6,726,708 B2 | 4/2004 | Lasheras | |
| 6,796,957 B2 * | 9/2004 | Carpenter et al. | 604/93.01 |
| 6,969,399 B2 * | 11/2005 | Schock et al. | 607/108 |
| 7,458,984 B2 * | 12/2008 | Yon et al. | 607/106 |
| 2003/0088299 A1 | 5/2003 | Magers et al. | |
| 2004/0267339 A1 * | 12/2004 | Yon et al. | 607/105 |

\* cited by examiner

TO FIG. 3B

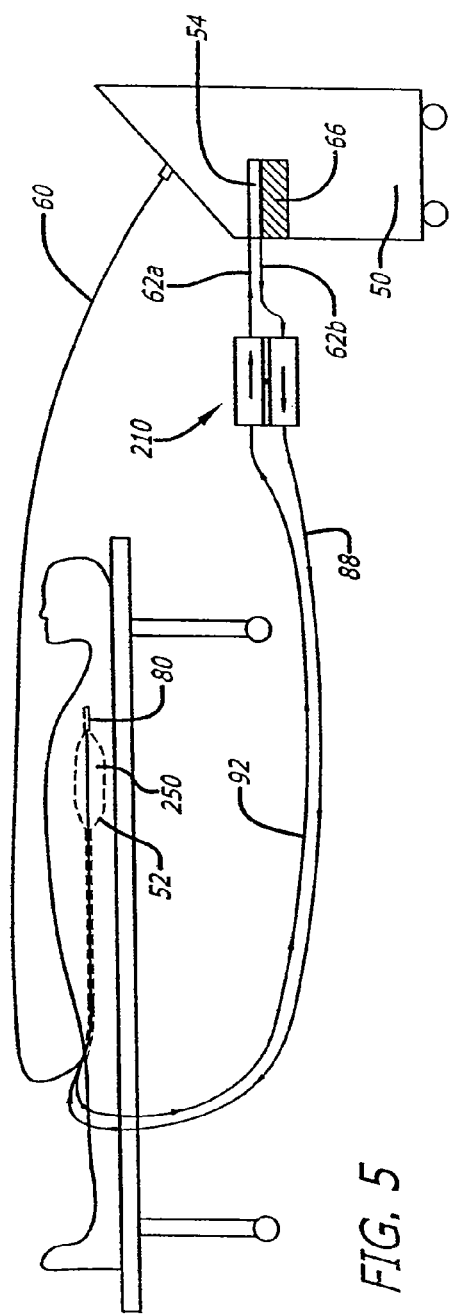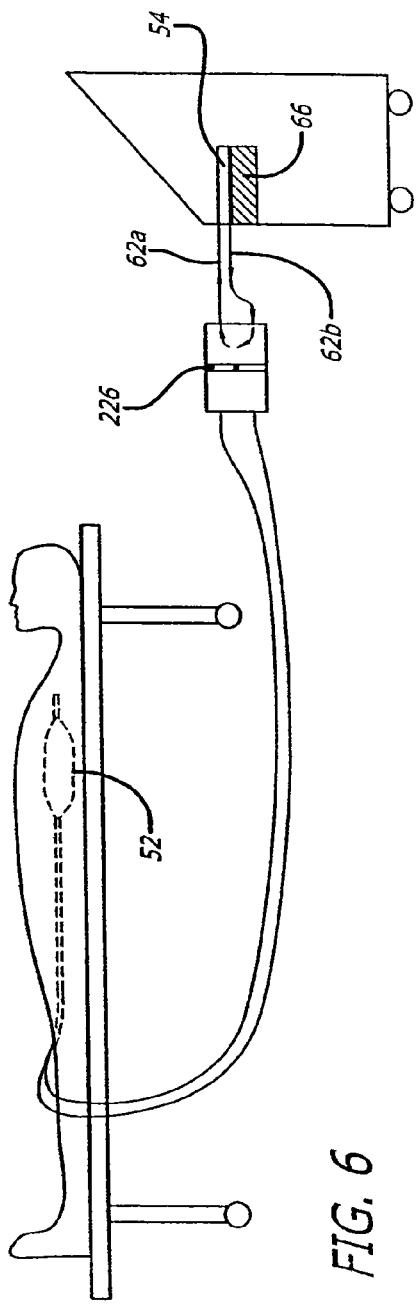
FIG. 5
FIG. 6

SYSTEM AND METHOD FOR DETERMINING AND CONTROLLING CORE BODY TEMPERATUE

CROSS-REFERENCES TO RELATED APPLICATIONS

This application is a continuation of Ser. No. 12/710,317, filed Feb. 22, 2010, now U.S. Pat. No. 8,100,957, issued Jan. 24, 2012, which is a continuation of Ser. No. 10/525,625, filed Oct. 3, 2005, now U.S. Pat. No. 7,666,215, issued Feb. 23, 2010, which is a 371 of PCT/US03/28683, filed Sep. 12, 2003, which claims priority to U.S. Provisional Application No. 60/410,096, filed Sep. 12, 2002, the entirety of which is incorporated herein by reference.

BACKGROUND

1. Field of the Invention

The present invention relates generally to medical devices and methods and, more particularly, to a programmable, microprocessor based controller and method for controlling the temperature and flow of a thermal exchange fluid that is circulated through a heat exchange catheter inserted into a patient's body for the purpose or cooling or warming at least a portion of the patient's body.

2. Description of Related Art

Under ordinary circumstances, the thermoregulatory mechanisms of a healthy human body serve to maintain the body at a constant temperature of about 37° C. (98.6° F.), a condition sometimes referred to as normothermia. To maintain normothermia, the thermoregulatory mechanisms act so that heat lost from the person's body is replaced by the same amount of heat generated by metabolic activity within the body. For various reasons such as extreme environmental exposure to a cold environment or loss of thermoregulatory ability as a result of disease or anesthesia, a person may develop a body temperature that is below normal, a condition known as hypothermia. A person may develop a condition that is above normothermia, a condition known as hyperthermia, as a result of extreme exposure to a hot environment, or malfunctioning thermoregulatory mechanisms, the latter being a condition sometimes called malignant hyperthermia. The body may also establish a set point temperature (that is, the temperature which the body's thermoregulatory mechanisms function to maintain) that is above normothermia, a condition usually referred to as fever.

Accidental hypothermia is generally a dangerous condition that may even be life threatening, and requires treatment. If severe, for example where the body temperature drops below 30° C., hypothermia may have serious consequences such as cardiac arrhythmias, inability of the blood to clot normally, or interference with normal metabolism. If the period of hypothermia is extensive, the patient may even experience impaired immune response and increased incidence of infection.

Simple methods for treating accidental hypothermia have been known since very early times. Such methods include wrapping the patient in blankets, administering warm fluids by mouth, and immersing the patient in a warm water bath. If the hypothermia is not too severe, these methods may be effective. However, wrapping a patient in a blanket depends on the ability of the patient's own body to generate heat to re-warm the body. Administering warm fluids by mouth relies on the patient's ability to swallow, and is limited in the temperature of the liquid consumed and the amount of fluid that may be administered in a limited period of time. Immersing a patient in warm water is often impractical, particularly if the patient is simultaneously undergoing surgery or some other medical procedure.

More recently, hypothermia may be treated in a more complex fashion. Heated warming blankets may be applied to a patient or warming lamps that apply heat to the skin of the patient may be used. Heat applied to the patient's skin, however, has to transmit through the skin by conduction or radiation which may be slow and inefficient, and the blood flow to the skin may be shut down by the body's thermoregulatory response, and thus, even if the skin is warmed, such mechanisms may be ineffective in providing heat to the core of the patient's body. When breathing gases are administered to a patient, for example a patient under anesthesia, the breathing gases may be warmed. This provides heat relatively fast to the patient, but the amount of heat that can be administered without injuring the patient's lungs is very limited. An alternative method of warming a hypothermic patient involves infusing a hot liquid into the patient via an IV infusion, but this is limited by the amount of liquid that can be infused and the temperature of the liquid.

In extreme situations, a very invasive method may be employed to control hypothermia. Shunts may be placed into the patient to direct blood from the patient through an external machine such as a cardiopulmonary by-pass (CPB) machine which includes a heater. In this way, the blood may be removed from the patient, heated externally, and pumped back into the patient. Such extreme measures have obvious advantages as to effectiveness, but also obvious drawbacks as to invasiveness. The pumping of blood through an external circuit that treats the blood is generally quite damaging to the blood, and the procedure is only possible in a hospital setting with highly trained personnel operating the equipment.

Accidental hyperthermia may also result from various conditions. Where the normal thermoregulatory ability of the body is lost, because of disease or anesthesia, run-away hyperthermia, also known as malignant hyperthermia, may result. The body may also set a higher than normal set point resulting in fever which is a type of hyperthermia. Like hypothermia, accidental hyperthermia is a serious condition that may sometimes be fatal. In particular, hyperthermia has been found to be neurodestructive, both in itself or in conjunction with other health problems such as traumatic brain injury or stroke, where a body temperature in excess of normal has been shown to result in dramatically worse outcomes, even death.

As with hypothermia, when the condition is not too severe, simple methods for treating the condition exist, such as cold water baths and cooling blankets, or antipyretic drugs such as aspirin or acetaminophen, and for the more extreme cases, more effective but complex and invasive means such as cooled breathing gases, cold infusions, and blood cooled during CPB also exist. These, however, are subject to the limitations and complications as described above in connection with hypothermia.

Although both hypothermia and hyperthermia may be harmful and require treatment in some cases, in other cases hyperthermia, and especially hypothermia, may be therapeutic or otherwise advantageous, and therefore may be intentionally induced. For example, periods of cardiac arrest or cardiac insufficiency in heart surgery result in insufficient blood to the brain and spinal cord, and thus can produce brain damage or other nerve damage. Hypothermia is recognized in the medical community as an accepted neuroprotectant and therefore a patient is often kept in a state of induced hypothermia. Hypothermia also has similar advantageous protective ability for treating or minimizing the adverse effects of certain neurological diseases or disorders such as head trauma, spinal trauma and hemorrhagic or ischemic stroke. Therefore it is sometimes desirable to induce whole-body or regional hypothermia for the purpose of facilitating or minimizing adverse effects of certain surgical or interventional procedures such as open heart surgery, aneurysm repair surgeries, endovascular aneurysm repair procedures, spinal surgeries, or other surgeries where blood flow to the brain, spinal cord or vital organs may be interrupted or compromised. Hypothermia has even been found to be advantageous to protect cardiac muscle tissue after a myocardial infarct (MI). Controlled reduction in body temperature may also be advantageous in treating and/or preventing other maladies, including ischemic or toxic damage to body tissues and organs, such as, for example, to minimize the toxic effect on the kidneys of contrast agents used during various diagnostic procedures.

Current methods of attempting to induce hypothermia generally involve constant surface cooling, by cooling blanket or by alcohol or ice water rubs. However, such cooling methods are extremely cumbersome, and generally ineffective to cool the body's core. The body's response to cold alcohol or ice water applied to the surface is to shut down the circulation of blood through the capillary beds, and to the surface of the body generally, and thus to prevent the cold surface from cooling the core. If the surface cooling works at all, it does so very slowly. There is also an inability to precisely control the temperature of the patient by this method.

If the patient is in a surgical setting, the patient may be anesthetized and cooled by CPB as described above. Generally, however, this is only available in the most extreme situations involving a full surgical team and full surgical suite, and importantly, is only available for a short period of time because of the damage to the blood caused by pumping. Generally surgeons do not wish to pump the blood for periods longer than 4 hours, and in the case of stroke or traumatic brain damage, it may be desirable to induce hypothermia for longer than a full day. Because of the direct control of the temperature of a large amount of blood, this method allows fairly precise control of the patient's temperature. However, it is this very external manipulation of large amounts of the patient's blood that makes long-term use of this procedure very undesirable.

Means for effectively adding heat to the core of the body that do not involve pumping the blood with an external, mechanical pump have been suggested. For example, a method of treating hypothermia or hyperthermia by means of a heat exchange catheter placed in the bloodstream of a patient was described in U.S. Pat. No. 5,486,208 to Ginsburg, the complete disclosure of which is incorporated herein by reference. Means of controlling the temperature of a patient by controlling such a system is disclosed in U.S. Pat. No. 5,837,003, also to Ginsburg, the complete disclosure of which is incorporated herein by reference. A further system for such controlled intervascular temperature control is disclosed in publication WO OO/10494 to Ginsburg et al., the complete disclosure of which is incorporated herein by reference. Those patents and publication disclose a method of treating or inducing hypothermia by inserting a heat exchange catheter having a heat exchange area into the bloodstream of a patient, and circulating heat exchange fluid through the a heat exchange balloon while the balloon is in contact with the blood to add or remove heat from the bloodstream. (As used herein, a balloon is a structure that may be readily inflated by increasing pressure in the balloon and collapsed by reducing pressure in the balloon vacuum.)

A patient's core body temperature can fluctuate unpredictably with the insertion of various medical devices within the patient's body during a medical procedure that can skew the reading of the body temperature when taken in the immediate area of the lumen where the medical device is inserted. Although current medical devices on the market include thermal or temperature sensors mounted directly on the device itself for measurement of the temperature within the body lumen (i.e., a catheter, an electrode on a catheter shaft, etc.), these types of medical devices only measure the temperature of the fluid in the vessel in the immediate area of the inserted device. Further, the placement of the temperature sensor on the catheter used to treat or control the patient's body core temperature puts the sensor in a position where the blood or other body fluid is perturbed by the catheter. For example, cooling or heating fluid flowing through the catheter to a heat exchange device mounted on the distal end of the catheter may slightly heat or cool the body fluid flowing past the body of the catheter upstream of the temperature sensor, resulting in biased temperature readings when the slightly warmed or cooled body fluid reaches the temperature sensor compared to core body temperature as determined by the average blood temperature. Such a bias may result in undershooting the target temperature when the biased temperature readings are used to control heating or cooling of the blood of the patient. This inability to control the patient's body core temperature during a medical procedure because of the devices' difficulty in obtaining an accurate measure of a patient's blood temperature may result in reduced treatment effectiveness if the patient's core temperature is heated or cooled beyond a target temperature.

Although heat exchange catheters, such as described above, provide a rapid and effective means to add or remove heat to a patient's blood to control the body temperature of the patient, accurate control of the temperature of the heat exchange fluid circulating within the heat exchange catheter is necessary to prevent too rapid heating or cooling, or over or under shooting of the target patient temperature sought to be obtained. Various attempts to measure the patient's body temperature during the heat exchange procedure have been attempted. For example, in one method, a temperature probe is inserted in the patient's esophagus and the signal from the temperature probe is communicated to a controller which adjusts the energy being added to or withdrawn from the heat exchange fluid circulating within the heat exchange catheter accordingly. While the esophageal temperature obtained is typically a reasonably accurate measurement of the patient's core temperature, inaccuracies may occur due to improper placement of the probe. Further, placement of the esophageal temperature probe is time consuming, requires precision in placing the probe in the proper area of the esophagus, and also may interfere with other tubes or catheters that may need to be inserted either through the patient's mouth or nasal passage.

Temperature probes, such as thermistors or thermocouples, have been located within the heat exchange catheter itself to provide a temperature signal to the controller. In this method, it is necessary to periodically stop the flow of fluid through catheter so that the fluid temperature may equilibrate with the temperature of the blood flowing outside of the catheter. Various methods of reducing the amount of time the fluid flow is stopped have also been attempted so that the fluid stoppage does not adversely affect the targeted rate of cooling or heating, nor allow the natural heating of the body to occur which would negate the desired benefit of the induced hypothermia.

One such apparatus and method is described in publication WO 03/015673, entitled "System and Method for Patient Temperature Control Employing Temperature Projection Algorithm", the disclosure of which is incorporated herein by reference in its entirety. A principle disadvantage of this method is that each time the flow is stopped, the maximum heating or cooling rate is decreased. Moreover, if the interval before the first stoppage is lengthened to speed heating or cooling, the method provides increased risk of overcooling or overheating unless the pump is stopped and the patient's temperature is confirmed. Additionally, when using algorithms to project the actual blood temperature, the fluid flow may never be stopped long enough for the heat exchange fluid to equilibrate with the actual blood temperature, thus providing only an estimate, and not an actual measurement, of the blood temperature.

Another method used has been to locate the temperature probe on the exterior surface of the heat exchange catheter, typically slightly distal to the heat exchange balloon. Such arrangements, however, typically provide fluctuating temperature signals to the controller, which may adversely affect the controller's ability to accurately determine the temperature of the patient's blood. The fluctuating signal is a result of the placement of the temperature sensor in the blood stream. As the blood flows around the heat exchange catheter, the flow of blood tends to separate into a cooler layer immediately adjacent the catheter and a warmer layer further away from the catheter. The situation is reversed if the catheter is being used to warm the patient. As the blood mixes as it flows downstream, the temperature sensor may be exposed to temperature fluctuations caused by incomplete mixing of the blood, which are detected by the sensors, resulting in a fluctuating temperature signal.

For the foregoing reasons, there is a need for an improved heat exchange system that provides for more accurate temperature measurement for use in controlling a heating/cooling means that warms or chills fluid that is then circulated through a heat exchange catheter. Such a system should be capable of estimating the actual core temperature of a patient's body from direct temperature measurement of the patient's blood, and should also be capable of identifying events, such as a change in heating or cooling parameters, a loss of a supplemental warming device, such as a heating blanket, or onset of shivering by the patient that may affect the control of the heating or cooling of the patient. Moreover, such a system should be capable of achieving such an estimate while minimizing or eliminating the interruption of fluid flow through the heat exchange catheter. The present invention fulfills these needs and others.

SUMMARY OF THE INVENTION

The invention provides for modification and control of the temperature of a patient, or selected portions of a patient, including controllably inducing a state of hypothermia in the patient. The invention also provides for controllably warming a patient in whom a state of reduced temperature, or hypothermia, has been induced.

In a general aspect, the present invention is embodied in a system and method for measuring a patient's temperature, and applying one or more analysis methods to the temperature data resulting from that measurement to smooth data to more closely approximate the actual temperature of blood flowing downstream of a heat exchange catheter, and using the results of that analysis to control the addition or removal of heat from a heat exchange medium circulating within the heat exchange catheter to warm or cool the patient's body to a selected target temperature.

In one aspect, the present invention is embodied in a method for measuring body temperature while regulating the temperature of at least a portion of a patient using a heat exchange catheter inserted into a lumen of the patient's body, the heat exchange catheter having conduits that enable circulation of a heat exchange medium between a heat exchange portion of the catheter and a heating/cooling apparatus for adding or removing thermal energy from the heat exchange fluid, the heating/cooling apparatus controlled by a controller, the method comprising providing a temperature probe to measure the temperature of the patient, the temperature probe providing a signal representative of the temperature of the patient to the controller, circulating fluid under control of the controller between the heat transfer catheter and the heating/cooling apparatus so as to regulate the temperature of patient, stopping the flow of fluid through the heat transfer catheter for a selected period of time, determining the temperature change while the fluid flow is stopped, comparing the temperature change while the fluid flow is stopped to a target temperature, and controlling the heating/cooling apparatus in accordance with the comparison to controllably add or remove thermal energy from the heat exchange fluid to heat or cool the patient's blood such that the patient's body temperature is substantially the same as the target temperature. In one embodiment, the circulating fluid is interrupted by stopping a fluid pump. In another embodiment, the flow of circulating fluid is substantially slowed by slowing the pumping speed of the pump. In yet another embodiment, the circulating fluid is diverted by a diverter valve.

In another aspect, the present invention includes a method for measuring body temperature while regulating the temperature of at least a portion of a patient, comprising providing a temperature probe having sensors to measure the temperature of patient, providing a disposable heat transfer catheter and heat exchange unit coupled via conduits and a diverter unit that enable controlled circulation of a heat exchange medium therebetween, providing a master control unit housing a microprocessor and a heater/cooler unit within, installing the heat exchange unit into the master control unit and into thermal communication with the heater/cooler unit, inserting the heat transfer catheter into the patient, circulating fluid between the heat transfer catheter and heat exchange unit in the master control unit, therein transferring heat between the heat exchange unit and the heater/cooler unit so as to regulate the temperature of the patient via the heat transfer catheter, periodically interrupting fluid flow from between the heat transfer catheter and the heat exchange unit, diverting the circulating fluid flow between the heat exchange unit and heater/cooler unit, bypassing the heat transfer catheter, monitoring the temperature of patient after a period time to determine an accurate core body temperature measurement, and re-starting the fluid circulation between the heat transfer catheter and the heat exchange unit.

In yet another aspect, one embodiment of the present invention includes a heat transfer catheter system, comprising a heat transfer catheter insertable into a patient, a disposable heat exchange unit having a fluid pathway therewithin and incorporating an integral pump head adapted to move fluid through the fluid pathway, conduits coupled to the heat transfer catheter and heat exchange unit that enable circulation of a heat exchange medium therebetween upon operation of the pump head, a diverter unit that periodically redirects the fluid pathway, bypassing the heat transfer catheter, and a reusable master control unit having a heater/cooler and a pump driver, the disposable heat exchange unit being adapted to couple to the master control unit such that the pump driver engages the integral pump head and so that the fluid pathway is in thermal communication with the heater/cooler.

In yet another aspect, the system of one embodiment of the present invention includes a controller having a microprocessor, the microprocessor programmed to receive a target temperature input and a sensor signal that represents a sensed patient temperature, the microprocessor also programmed and configured to provide signals to the heat exchanger to add heat to the heat exchange medium of a heat exchange catheter if the target temperature is above the patient temperature and remove heat from the heat exchange medium if the target temperature is below the patient temperature, and to periodically interrupt fluid circulation within the heat exchange unit and the heat transfer catheter, and wherein the microprocessor responds to the signal from the sensor with a proportional integrated differential (PID) response such that the rate at which patient temperature approaches the target temperature is controlled.

In still another aspect, another embodiment of the present invention includes a method for measuring body temperature while regulating the temperature of at least a portion of a patient using a heat exchange catheter inserted into a lumen of the patient's body, the heat exchange catheter having conduits that enable circulation of a heat exchange medium between a heat exchange portion of the catheter and a heating/cooling apparatus for adding or removing thermal energy from the heat exchange fluid, the heating/cooling apparatus controlled by a controller, comprising measuring the temperature of the patient using a temperature probe, the temperature probe providing a signal representative of the temperature of the patient to the controller, circulating fluid under control of the controller between the heat transfer catheter and the heating/cooling apparatus so as to regulate the temperature of patient, analyzing the temperature signals received from the temperature probe for a selected period of time to determine a peak temperature, comparing the determined peak temperature to a target temperature, and controlling the heating/cooling apparatus in accordance with the comparison to controllably add or remove thermal energy from the heat exchange fluid to heat or cool the patient's blood so that the determined peak temperature approaches the target temperature.

In yet another aspect, one embodiment of the present invention includes analyzing the temperature signals for a temperature sensor by sampling the signals at a predetermined interval, determining the highest temperature value sampled within a selected range of the predetermined intervals and storing that determined value in a memory of the controller, incrementing the selected range of predetermined intervals a selected number of times and, after each incrementing, repeating determining the highest temperature value sampled within the incremented selected range of predetermined intervals and storing that value, and calculating the peak temperature value from the stored determined values. In another embodiment, the lowest temperature value sampled is determined and used to calculate the peak temperature value.

In another aspect, an embodiment of the present invention includes calculating an offset value and adding the offset value to the peak temperature before comparing the peak temperature to the target temperature. In one embodiment, the offset value is a static value; in another embodiment, the offset value is a dynamic offset value. In still another embodiment, the offset value is calculated using a method incorporating the equation:

$$Offset_{RT} = \frac{Offset_{Calc} \cdot \ln|\Delta PF_{RT}|}{\ln|\Delta PF_{Calc}|}$$

where:
  $Offset_{RT}$=Dynamic real time offset
  $Offset_{Calc}$=Offset calculated when flow stopped; calculated as:

$$Offset_{Calc} = T_{Core} - T_{Peak}$$

where:
  $T_{Core}$=Temperature sensed after flow is stopped for a selected period and sensed temperature equilibrium is reached
  $T_{Peak}$=Temperature sensed just before flow is stopped
  $\Delta PF_{RT}$=Real time temperature differential between an instantaneous peak sensed blood temperature and the corresponding instantaneous temperature measurement of the heat exchange fluid
  $\Delta PF_{Calc}$=Temperature differential between the peak blood temperature sensed just before flow stoppage and the corresponding temperature of the heat exchange fluid measured at the same time.

In still another aspect, an embodiment of the present invention includes a system for regulating the temperature of at least a portion of a patient's body, comprising, a heating/cooling apparatus, a heat exchange catheter for insertion into a lumen of the patient's body, the heat exchange catheter having conduits that enable circulation of a heat exchange medium between a heat exchange portion of the catheter and the heating/cooling apparatus for adding or removing thermal energy from the heat exchange medium, a temperature sensor disposed in the lumen downstream of the heat exchange catheter for providing temperature signals representative of the temperature of body fluid flowing through the lumen, and a controller responsive to the temperature signals to control the heating/cooling apparatus to add or remove thermal energy from the heat exchange medium.

In another aspect, an embodiment of the present invention includes a processor and a memory, the processor capable of being programmed by software to sample the temperature signals at a predetermined interval, determine the a selected temperature value sampled within a selected range of the predetermined intervals and store that determined value in a memory of the controller, increment the selected range of predetermined intervals a selected number of times and, after each increment, repeating determining the selected temperature value sampled within the incremented selected range of predetermined intervals and store that value, and calculate a peak temperature value from the stored determined values.

A still further aspect of the present invention embodies a system for regulating the temperature of at least a portion of a patient's body, comprising a heating/cooling apparatus, a heat exchange catheter for insertion into a lumen of the patient's body, the heat exchange catheter having conduits that enable circulation of a heat exchange medium between a heat exchange portion of the catheter and the heating/cooling apparatus for adding or removing thermal energy from the heat exchange medium, a temperature sensor disposed in the lumen downstream of the heat exchange catheter for providing temperature signals representative of the temperature of body fluid flowing through the lumen, the temperature sensor configured to move within the lumen in response to the flow of body fluid within the lumen; and a controller responsive to the temperature signals to control the heating/cooling apparatus to add or remove thermal energy from the heat exchange medium.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 5 is a perspective view of a patient undergoing treatment using a system in accordance with an embodiment of the present invention incorporating a diverter valve to divert the flow of heat exchange fluid;

FIG. 6 is a perspective view of the embodiment depicted in FIG. 5 showing the diversion of fluid within the heat exchange circulation circuit;

FIG. 7A is a plan view of the embodiment of the diverter of FIG. 7 shown in the by-pass, or diversion circuit position;

DETAILED DESCRIPTION OF THE PREFERRED EMBODIMENTS

Figure 1:
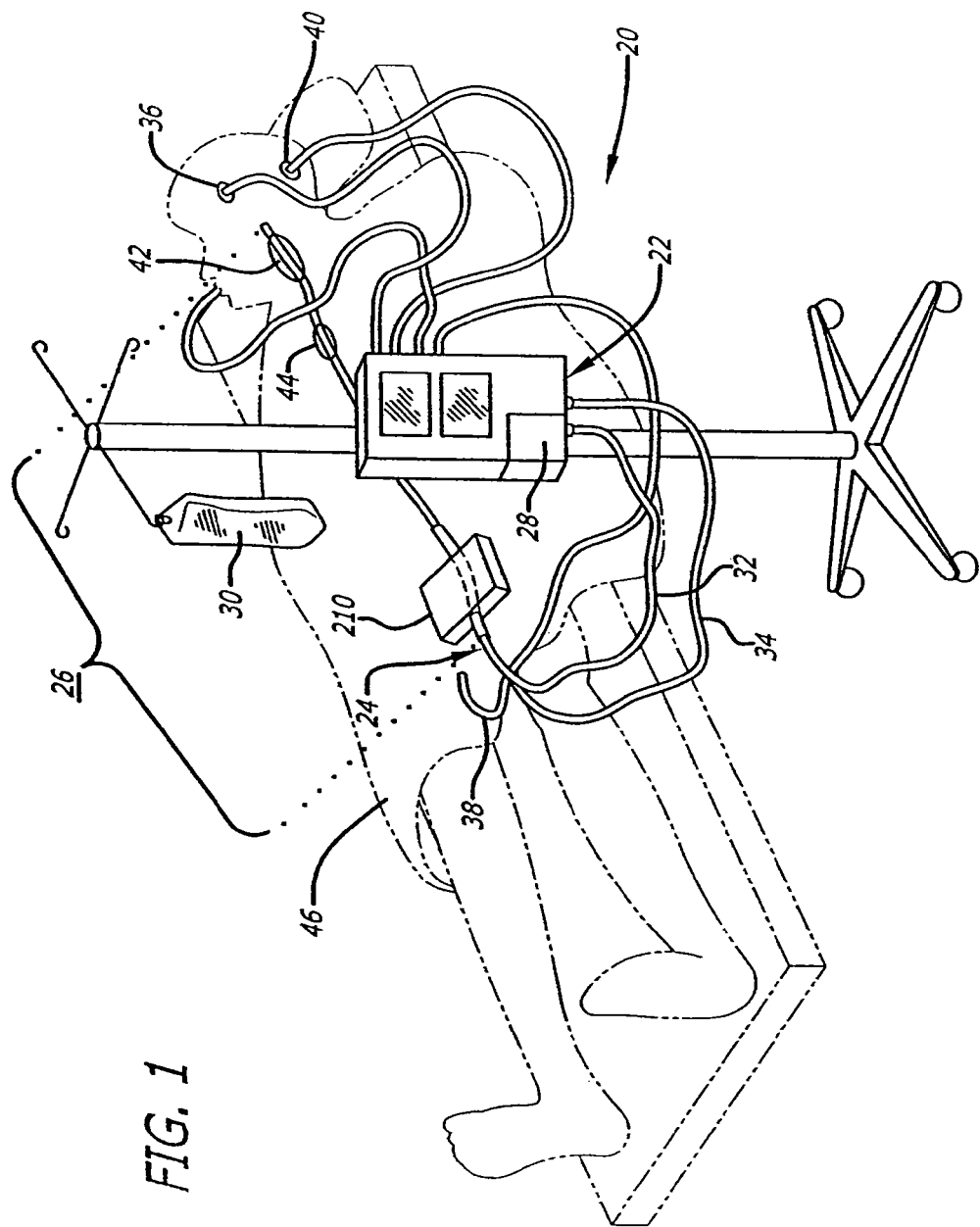
FIG. 1 is a perspective view of a patient undergoing treatment using a system in accordance with the present invention.

The present invention is a method of measuring body temperature while performing endovascular temperature control. The invention includes a catheter placed in the bloodstream of a patient for regulating the patient's body temperature, although those of skill in the art will understand that various other applications for the system of the present invention are possible. In a preferred application, one or more of the heat exchange catheters of the present invention are positioned within a patient's vasculature to exchange heat with the blood in order to regulate the patient's overall body temperature, or to regulate the temperature of a localized region of the patient's body. Heat exchange fluid is then circulated through the catheter to exchange heat between the blood and the heat exchange fluid, and a controller manages the functioning of the system periodically stopping circulation, if necessary, to achieve an accurate temperature measurement. The catheters may be, for example, suitable for exchanging heat with arterial blood flowing toward the brain to cool the brain, and may thus prevent damage to brain tissue that might otherwise result from a stroke or other injury, or cooling venous blood flowing toward the heart to cool the myocardium to prevent tissue injury that might otherwise occur following an MI or other similar event.

In general, the invention provides a control unit and method for controlling the temperature and flow of heat transfer fluid for a heat transfer catheter used for controlling the body temperature of a patient. The control unit initially supplies heat transfer fluid to the heat transfer catheter to prime the heat exchange catheter for use. It also receives input from the user, receives temperature information from sensors that sense patient temperature information, and based thereon, controls the temperature of the heat transfer fluid and the circulation of the heat transfer fluid within the heat exchange catheter. Further, based on the sensor feedback the heat transfer fluid may be stopped from flowing into the heat exchange catheter for an interval of time while the control unit monitors the core body temperature. The cassette and the controller, working together, can stop fluid flow, for example, by shutting down or slowing the pump motor or, alternatively, by diverting the heat exchange fluid into a diversion pathway that bypasses the heat exchange catheter. Alternatively, the system of the present invention may filter the temperature signals to smooth the measured temperature fluctuations caused by the presence of the catheter in the blood flow.

Overview of Heat Exchange System

Any suitable heat exchange catheter may be utilized in a heat exchange system for regulating the temperature of a patient or a region of the patient's body and controlled by the control unit as disclosed herein. In addition to the catheters disclosed herein, and by way of illustration and not of limitation, catheters that may be utilized in this invention are the catheters disclosed in U.S. Pat. No. 5,486,208 to Ginsburg, U.S. Pat. No. 5,837,003 to Ginsburg, WO 00/10494 to Ginsburg et al., and U.S. Pat. No. 5,624,392 to Saab, the complete disclosure of each of which is hereby incorporated herein by reference in its entirety.

One example of such a heat exchange catheter system 20 is shown in FIG. 1, and includes a catheter control unit 22 and a heat exchange catheter 24 formed with at least one heat transfer section 44. The heat transfer section or sections are located on that portion of the catheter 24, as illustrated by section 26, that is inserted into the patient. The catheter control unit 22 may include a fluid pump 28 for circulating a heat exchange fluid or medium within the catheter 24, and a heat exchanger component for heating and/or cooling circulating fluids within the heat transfer system 20. A reservoir or fluid bag 30 may be connected to the control unit 22 to provide a source of heat transfer fluid such as, saline, blood substitute solution, or other biocompatible fluid. A circulatory heat exchange flow channel within the catheter may be respectively connected to inlet 32 and outlet 34 conduits of the pump 28 for circulation of the heat transfer fluid through the balloon to cool the flow of fluid within a selected body region. A similar arrangement may be implemented for heating of selected body regions simultaneously or independently of each other using the heating component of the system.

The control unit 22 may further receive data from a variety of sensors which may be, for example, solid state thermocouples, thermistors or other temperature sensitive sensing devices, to provide feedback from the temperature of the heat exchange fluid in catheter. The feedback temperature signals may also be obtained from other sensors, either alone or in combination with the sensed temperature of the heat exchange fluid, to provide patient temperature information representing core temperature or temperature of selected organs or portions of the body. For instance, sensors may include a temperature probe 36 for the brain or head region, a rectal temperature probe 38, an ear temperature probe 40, an esophageal temperature probe (not shown), a bladder temperature probe (not shown), and sensors in the blood stream of the patient, and the like.

Based upon sensed temperatures and conditions, the control unit 22 may direct the heating or cooling of the catheter in response. The control unit 22 may activate a heat exchanger at a first sensed temperature to heat fluid which is then circulated through the balloon, and may also de activate the heat exchanger at a second sensed temperature which may be relatively higher or lower than the first sensed temperature or any other predetermined temperature. Alternatively, the control unit may actively control the heat exchanger to cool the heat exchange fluid to cool the balloon. The control unit 22 may operate multiple heat transfer units to independently heat or cool different selected heat transfer sections of the heat exchange catheter to attain desired or selected temperatures in different body regions. Likewise, the controller 22 may stop fluid flow to the heat exchanger for a selected period of time to control temperature at particular regions of the patient's body. The controller might also activate or de activate other apparatus, for example external heating blankets or the like, in response to sensed temperatures.

The regulation exercised over the heat transfer catheters or other devices may be a simple on off control, regulating the degree of heating or cooling and resulting ramp rates of heating or cooling, or proportional control as the temperature of the heat exchange region or patient approaches a target temperature, or may be a significantly more sophisticated control scheme including diverting fluid flow, or the like.

The catheter control unit 22 may further include a thermoelectric cooler and heater (and associated flow conduits) that are selectively activated to perform both heating and cooling functions with the same or different heat transfer mediums within the closed loop catheter system. For example, a first heat transfer section 42 located on the insertion portion 26 of at least one temperature regulating catheter 24 may circulate a cold solution in the immediate head region, or alternatively, within a carotid artery or other blood vessel leading to the brain. The head temperature may be locally monitored with temperature sensors 36 positioned at a relatively proximate exterior surface of the patient or within selected body regions. Another heat transfer section 44 of the catheter 24, also located on the insertion portion 26, may circulate a heated solution within a collapsible balloon or otherwise provide heat to other body locations through heat elements or other mechanisms described in accordance with other aspects of the invention. While heat exchange catheter 24 may provide regional hypothermia to the brain region for neuroprotective benefits, other parts of the body may be kept relatively warm so that adverse side effects such as discomfort, shivering, blood coagulopathies, immune deficiencies, and the like, may be avoided or minimized. Warming of the body generally below the neck may be further achieved by insulating or wrapping the lower body in a heating pad or blanket 46 while the head region above the neck is cool. It should be understood that multiple heat exchange sections of the catheter 24 may be modified to provide whole body cooling or warming to affect body core temperature.

Exemplary Heat Exchange System

The present invention contemplates the use of a re-usable controller or control console having a heater/cooler device therein and which receives a disposable heat exchange element, such as, for example, a cassette, coupled via conduits to a distal indwelling heat exchange catheter. More specifically, in one embodiment the controller desirably includes an outer housing having an opening or slot for receiving the heat exchange element therewithin, the opening and housing ensuring reliable positioning of the heat exchange element in proximity with the heater/cooler device. In this manner, set up of the system is facilitated because the operator only needs to fully insert and seat the heat exchange element into the controller opening in order to couple the re usable and disposable portions of the system. While the system is shown having a slot to receive the cassette, other arrangements are possible so long as the cassette is kept in close proximity to the heat exchange element.

Figure 2:
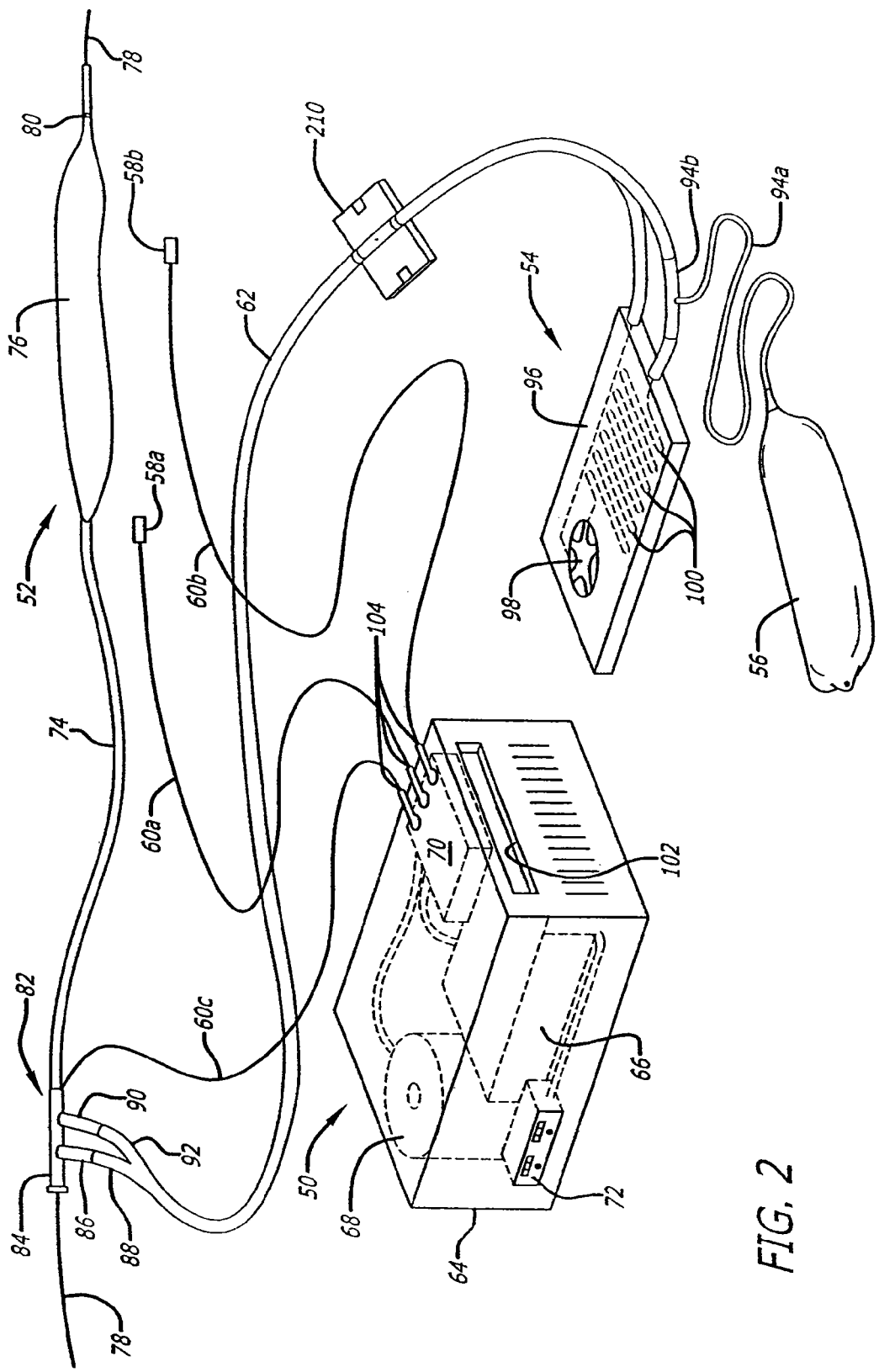
FIG. 2 is a schematic illustration of a disposable heat exchange cassette attached to a heat exchange catheter via a diverter unit and an external fluid source, and positioned for insertion into a suitable opening in are usable master control unit of the present invention.

In an exemplary embodiment, FIG. 2 illustrates a heat exchange catheter system that includes a re-usable catheter control unit 50 and a plurality of disposable components including a heat exchange catheter 52, a heat exchange element 54, a saline bag 56, sensors 58a, 58b and associated wires 60a, 60b, and a plurality of fluid flow conduits including a two way conduit 62 extending distally from the heat exchange element 54.

Alternatively, a sensor 80 may be positioned on the balloon or catheter outer surface in direct contact with the blood stream. A wire 60c from sensor 80 capable of communicating signals from sensor 80 extends through a lumen of the catheter towards the proximal end of the catheter. Once wire 60c exits from the proximal end of the catheter, it may be connected to the controller 50. In this manner, signals representative of the temperature of the blood at a location distal of a heat exchange 76 may be communicated to the controller 50, and used by the controller 50 to control a heating/cooling element 66 to add or remove energy from the heat exchange fluid to heat, cool or maintain the temperature of the blood flowing past heat exchanger 76. Alternatively, sensor 80 may be disposed on a wire that is extended through a port in the heat exchange catheter located distally of the heat exchanger 76. In this manner, sensor 80 would not be mounted on the heat exchanger 76 or catheter, but would be separate therefrom, allowing the position of sensor 80 relative to the heat exchanger 76 to be adjusted as needed during treatment of the patient.

It will be understood by those skilled in the art that many different configurations are possible for mounting temperature sensors to the catheter. For example, in one embodiment, the temperature sensor may be integrated into the catheter itself, either formed or mounted within the catheter casing. Alternatively, the temperature sensor may be a separate component that is removably mounted to the catheter. The temperature sensor may be located at the very distal end of the catheter, or a sensor or sensors may be mounted at a selected location or locations along the length of the catheter that is inserted within the lumen of the blood vessel.

In yet another embodiment, a temperature sensor may be inserted through a lumen of the catheter and positioned beyond the catheter into the blood stream. In this manner, the sensor is isolated from any contact with the catheter itself, and floats freely in the blood stream. In one embodiment, the sensor is positioned distal to the end of the catheter. In another embodiment, the sensor may be positioned proximally to the distal end of the catheter.

In another embodiment, a sensor probe may incorporate a tip shape that interacts with the blood flowing past the sensor to cause the sensor to sweep across a wider cross-section of the vessel. In one embodiment, such a sensor has a tip with a helical shape that causes the tip to revolve within the vessel as the blood flows past and through the tip. While such a design may increase the temperature fluctuations sensed by the sensor, when the fluctuating temperature signals are analyzed in accordance with the methods set forth herein, the result would actually improve the correlation between measured temperature and core body temperature.

It should be understood that the term "distal," as applied to the catheter, refers to the part of the catheter that is inserted furthest into the patient's body. While the location of the temperature sensor has been discussed with reference blood flowing from a proximal area of the catheter towards the distal end of the catheter, it should be understood that the inventions described herein are equally useful where the catheter is inserted in a vessel such that blood flows from the distal end of the catheter towards a proximal portion of the catheter.

The re usable catheter control unit 50 includes an outer housing 64 within which is provided the heater/cooler 66, a pump driver 68, and a controller processor 70. The controller processor is typically a microprocessor having sufficient processing speed and capacity to monitor and analyze user inputs and sensor signals and to control the heater/cooler 66 and pump driver 68. In addition, a fluid diverter 210 may control fluid flow to the catheter 52 in response to control signals provided to it by the controller processor 70.

Typically, the controller processor 70 may be programmed using either custom software or programs stored in read only memory or random access memory. These programs may be changed or updated as necessary to refine control of the heater/cooler and pump driver, or to add new or additional processing features or capabilities to the controller processor 70.

A manual input unit 72 enables an operator to enter desirable operating parameters of the controller, for example a pre selected temperature, or target temperature, for patient's body or a selected organ or portion of the patient's body, such as the brain, heart, kidneys and the like. Each of the electronic devices provided within the control unit 50 communicate through suitable wiring.

The heat exchange catheter 52 is formed with a catheter flow line 74 and a heat exchanger 76 which may be, for example, a heat exchange balloon operated using a closed loop flow of a biocompatible fluid that serves as the heat exchange medium. The catheter 52 may include a working lumen (not shown) for injection of drugs, fluoroscopic dye, or the like, and for receipt of a guide wire 78 for use in placing the catheter at an appropriate location in the patient's body. As stated previously, sensor 80 may be provided on the catheter 52 distal to the heat exchanger 76 to monitor the temperature of blood flowing past the heat exchange balloon or the sensor may be separated from the catheter and positioned distal to the distal end of the catheter. Additionally, other sensors may be provided as desired to monitor the blood temperature at the distal tip of the catheter, at the proximal tip of the balloon, or at any other desired location along the catheter.

The proximal end of the catheter flow line 74 may be connected to a multi arm adapter 82 for providing separate access to various channels in the catheter 52. For example, a first arm 84 may provide access to the working lumen of the catheter 52 for insertion of the guide wire 78 to steer the heat exchange catheter to the desired location. Where the heat exchanger 76 is a heat exchange balloon for closed loop flow of a heat exchange medium, the adapter 82 may contain a second arm 86 connected to an inflow line 88, and a third arm 90 connected to an outflow line 92. The inflow line 88 and outflow line 92 are therefore placed in flow communication with respective inflow and outflow channels (not shown) provided in the flow line 74 and heat exchanger 76. In this regard, the inflow and outflow lines 88, 92 may come together to form the single dual channel flow line 62 connected to the heat exchange element 54. Furthermore, an external fluid source such as the saline bag 56 may be placed in fluid communication with the outflow line 92 via a conduit 94a and a T junction 94b.

In the exemplary embodiment, inflow line 88 and outflow line 92 are attached to a diverter 210. The diverter 210 is controlled by the controller 50 to enable the flow of heat exchange fluid to the catheter to be interrupted by diverting the flow of the fluid back through the heat exchange element 54 before the fluid can flow into line 88. The external fluid source may be used when needed to prime the closed loop heat exchange balloon system. Alternatively, the external fluid source may be directly connected to the heat exchange unit 54.

Still with reference to FIG. 2, the heat exchange unit 54 desirably includes a heat exchange plate 96 and a pump head 98. The pump head 98 pumps heat exchange fluid through a serpentine fluid pathway 100 in the heat exchange plate 96, and through the associated flow lines and catheter 52. As mentioned, the heat exchange unit 54 is configured to install into the re usable catheter control unit 50. In this regard, the heat exchange unit 54 is desirably plate shaped and sized to fit through an elongate slot 102 in the control unit housing 64. Once inserted, the pump head 98 is placed in proximity to and engaged with the pump driver 68, and the heat exchange plate 96 is placed in proximity to and in thermal communication with the heater/cooler 66. The controllable pump driver 68 may periodically stop and start fluid circulation.

A solid state thermoelectric heater/cooler 66 is particularly advantageous when used to provided heating and cooling to the heat exchange fluid because the same unit is capable of either generating heat or removing heat by simply changing the polarity of the current activating the thermoelectric heater/cooler. Therefore, the heater/cooler 66 may be conveniently controlled so as to supply or remove heat from the system without the need for two separate units.

The pump driver 68 engages and activates the pump head 98 to cause it to circulate heat exchange fluid through the heat exchange unit 54 and the serpentine path 100 in the heat exchange plate 96. Therefore, when the heat exchanger unit 54 is properly installed in the control unit 50, the heater/cooler 66 may act to heat or cool the heat exchange fluid as that fluid is circulated through the serpentine pathway 100 and thereafter through the flow lines leading to the in dwelling heat exchanger 76. When the heat exchange fluid is circulated through the heat exchanger 76 located in the patient's body, it may act to add or remove heat from the body. In this way, the heater/cooler 66 regulates the blood temperature of the patient as desired. While pump driver 68 and pump head 98 are depicted as being mechanically coupled, it will be understood that driver 68 and pump head 98 may also be electrically coupled. Additionally, pump head 98 may include a small motor capable of driving the pump head and which receives its motive force from pump driver 68.

The heater/cooler 66 and pump driver 68 are responsive to the controller processor 70. The processor 70 receives data input through electrical connections 104 to numerous sensors, for example body temperature sensors 58a, 58b positioned to sense the temperature at various locations within the patient. For example, the temperature may be sensed at the patient's ear, brain region, bladder, rectum, esophagus, or other appropriate location as desired by the operator. Also, as mentioned, a sensor 80 may monitor the temperature of the heat exchanger 76 or alternatively, when sensor 80 is positioned distal to the heat exchanger, the temperature of blood after it has flowed past the heat exchanger 76. Alternatively, particularly where the blood flows from distal to proximal with reference to the catheter, sensor 80 may be positioned to measure the temperature of the blood before it flows past the heat exchanger. Other sensors along the catheter 52 may also provide input to the controller processor 70, such as via a wire 60c. Additionally, by means of the manual input unit 72, an operator provides the operating parameters of the control system such as, for example, a pre selected temperature for the brain and/or the whole body of the patient. The operator input parameters are communicated to the controller processor 70 by means of appropriate wiring.

The controller processor 70 coordinates the various data received and selectively actuates the several operational subsystems to achieve and maintain desired results; i.e., proper measurement and regulation of the patient's body temperature. For example, the processor 70 may actuate the heater/cooler 66 to increase the amount of heat it is removing from the heat exchange fluid if the actual temperature of the patient is above the specified, or target, temperature, or it may decrease the amount of heat being removed from the heat exchange fluid if the temperature of the patient is below the specified temperature.

Alternatively, the processor 70 may regulate the flow of heat exchange fluid to the heat exchanger in the blood stream by, for example, slowing the pump or stopping the pump altogether for a selected period of time or until the controller receives a signal indicating that pumping should be resumed. For example, the pumping of the heat exchange fluid may be stopped when the sensed body or regional temperature reaches the desired temperature, and then pumping may be re-started after a period of time or when the sensed temperature rises or falls from the target temperature sufficiently to require restarting the pump. As will be discussed in more detail below, the processor 70 may also stop the pumping of heat exchange fluid through the catheter periodically to improve the accuracy of measurement of the temperature of the patient's blood, either by activating diverter 210 or by sending a signal to the pump driver 68 to stop or reduce the speed of the pump, resulting in little, if any, flow of heat exchange fluid through the catheter.

Referring still to FIG. 2, the disposable heat exchange unit 54 of the invention is shown as being attached to a heat exchange catheter 52 via the fluid diverter 210, and external fluid source 56 is positioned in cooperation with a suitable reusable master control unit 50. Prior to commencing treatment, the heat exchange unit 54 is inserted into the reusable master control unit 50, the external fluid source 56 is attached to the fill port and the pump 98 is automatically or passively primed and the disposable system filled, after which the catheter is ready for insertion in the vasculature of the patient, for example in the inferior vena cava or the carotid artery. Chilled or warmed biocompatible fluid, such as saline, is pumped into the closed circuit catheter which exchanges heat directly with the patient's blood. The control unit serves to automatically control the patient's temperature. Once treatment with the catheter is complete, the catheter is removed from the patient and the cassette is removed from the reusable master control unit. Both the catheter and cassette, along with the diverter unit may then be discarded. The reusable master control unit, however, which never comes into direct contact with the heat exchange fluid, is ready for immediate use for treatment on other patients, along with a new cassette and catheter and fresh external fluid source.

Exemplary Method of Temperature Control

Figure 3A:
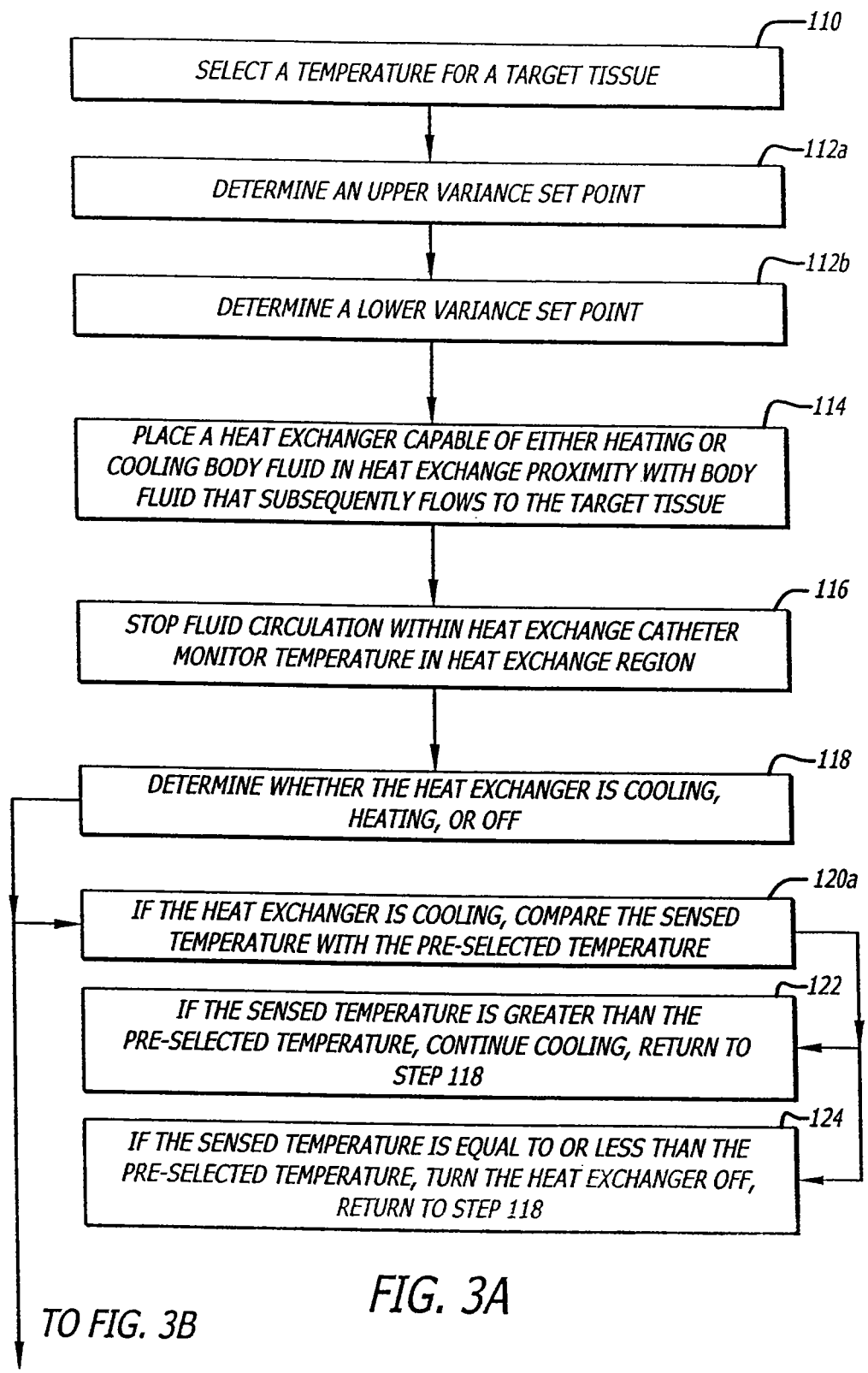
FIGS. 3A 3B together show a flowchart of a control scheme of an embodiment of the heat exchange system of the present invention.
Figure 3:
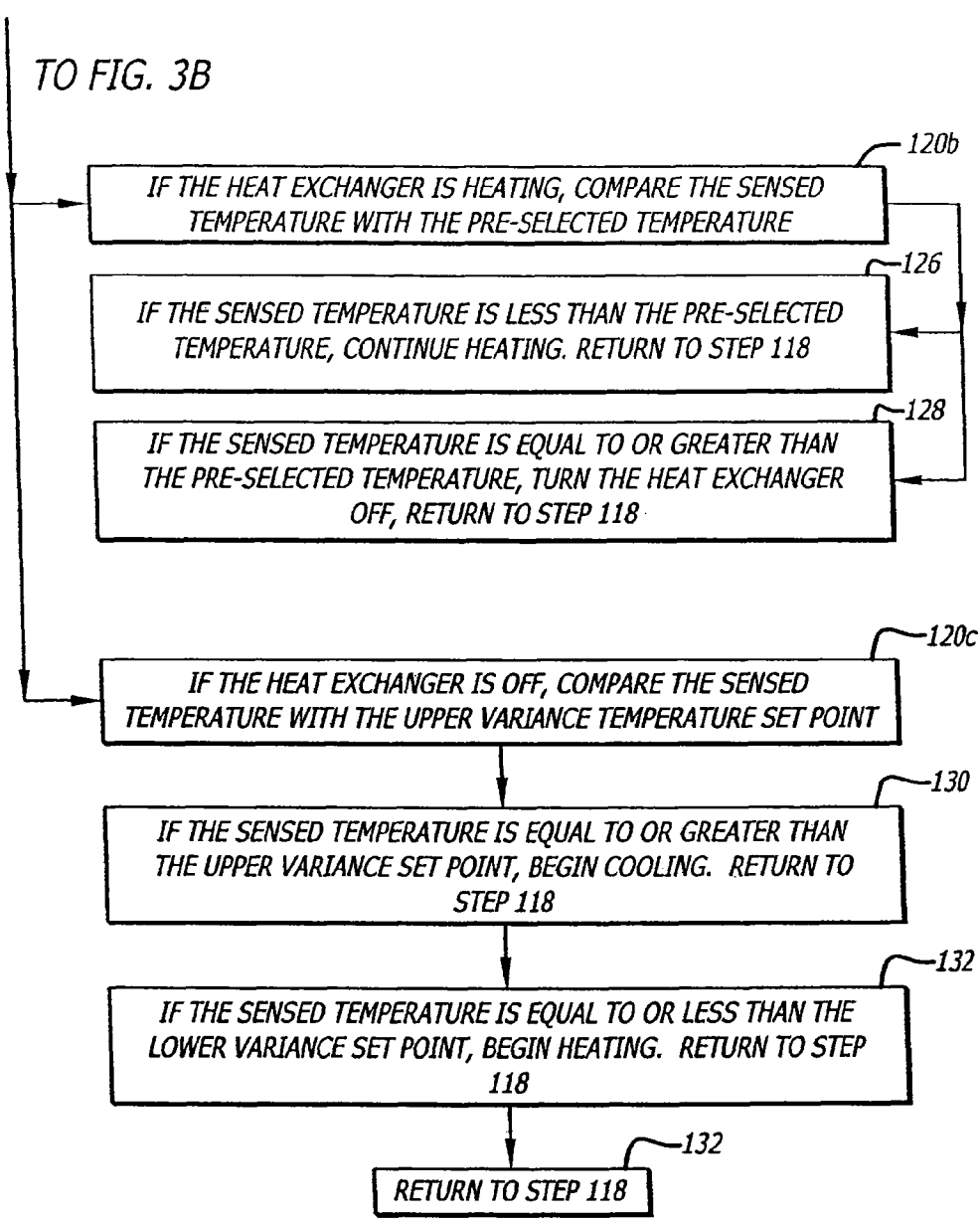

The flowchart seen in FIGS. 3A and 3B illustrates an exemplary sequence of steps that the controller processor 70 coordinates during temperature regulation of a patient. First, in step 110, a target temperature for the target tissue (which may be the entire body) is selected, generally by user input. Steps 112a and 112b involve determination of an upper variance set point and a lower variance set point, respectively. This is generally a pre set buffer range above and below the target temperature that is built or programmed into the controller processor. These variance set points straddle the target temperature and create a buffer range of temperature within which the controller operates.

More specifically, the sensed temperature for the target tissue is obtained in step 114a prior to or after step 116 in which a heat exchanger capable of either heating or cooling body fluid is placed in proximity with body fluid that subsequently flows to the target tissue. Based on user input, or on a comparison between the target temperature and the sensed tissue temperature, a determination is made in step 118 as to whether the heat exchanger will be operating a cooling mode, a heat mode, or will remain off. That is, if the target temperature equals the tissue temperature then there will be no need to initially heat or cool the body fluid.

The determination step 118 leads to three different modes of operation of the system, depending on whether the system will be COOLING, HEATING, or OFF. These modes of operation correspond to steps 120a, 120b, and 120c, which appear on both the FIGS. 3A and 3B, however, these modes of operation may be preceded by a stoppage of the circulating fluid in order to obtain equilibrated temperature measurements at the targeted tissue area, as previously described. It should be noted that while the operation of the heat exchanger is described as having an OFF mode, a thermoelectric heat exchanger will generally not be in an off mode unless the system is powered down. Instead, where the temperature is to be maintained, the thermoelectric device will be controlled to cycle between heating and cooling modes as required.

If the system is in the COOLING mode, the flowchart logic leads to step 120a which compares the sensed tissue temperature with the pre selected target temperature. If the tissue temperature is greater than the target temperature, the system continues cooling as indicated in step 122, and the processor 70 returns to decision step 118. On the other hand, if the sensed tissue temperature is equal to or less than the target temperature, the heat exchanger is converted to the OFF to HEATING mode as indicated in step 124 and the processor 70 returns to decision step 118.

If the system is in the HEATING mode, the flowchart logic leads to step 120b which also compares the sensed tissue temperature with the pre selected target temperature. If the tissue temperature is less than the target temperature, the system continues heating as indicated in step 126, and the processor 70 returns to decision step 118. On the other hand, if the tissue temperature is equal to or greater than the target temperature, the heat exchanger is converted to the OFF or COOLING mode as indicated in step 128, and the processor 70 returns to decision step 118.

If the system is in the OFF mode, the flowchart logic leads to step 120c which compares the sensed tissue temperature with the upper variance temperature set point. Then, if the sensed tissue temperature is equal to or greater than the upper variance set point, the system is converted to the COOLING mode as indicated in step 130, and the processor 70 returns to decision step 118. If the tissue temperature is less than the upper variance set point, the processor continues to step 132 in the flowchart logic, and determines if the tissue temperature is equal to or less than the lower variance set point, whereby the system is converted to the HEATING mode and processor 70 returns to decision step 118. Finally, if the tissue temperature is between the upper and lower variance set points, the system does nothing as indicated in step 134, and the processor 70 returns to decision step 118.

Figure 4:
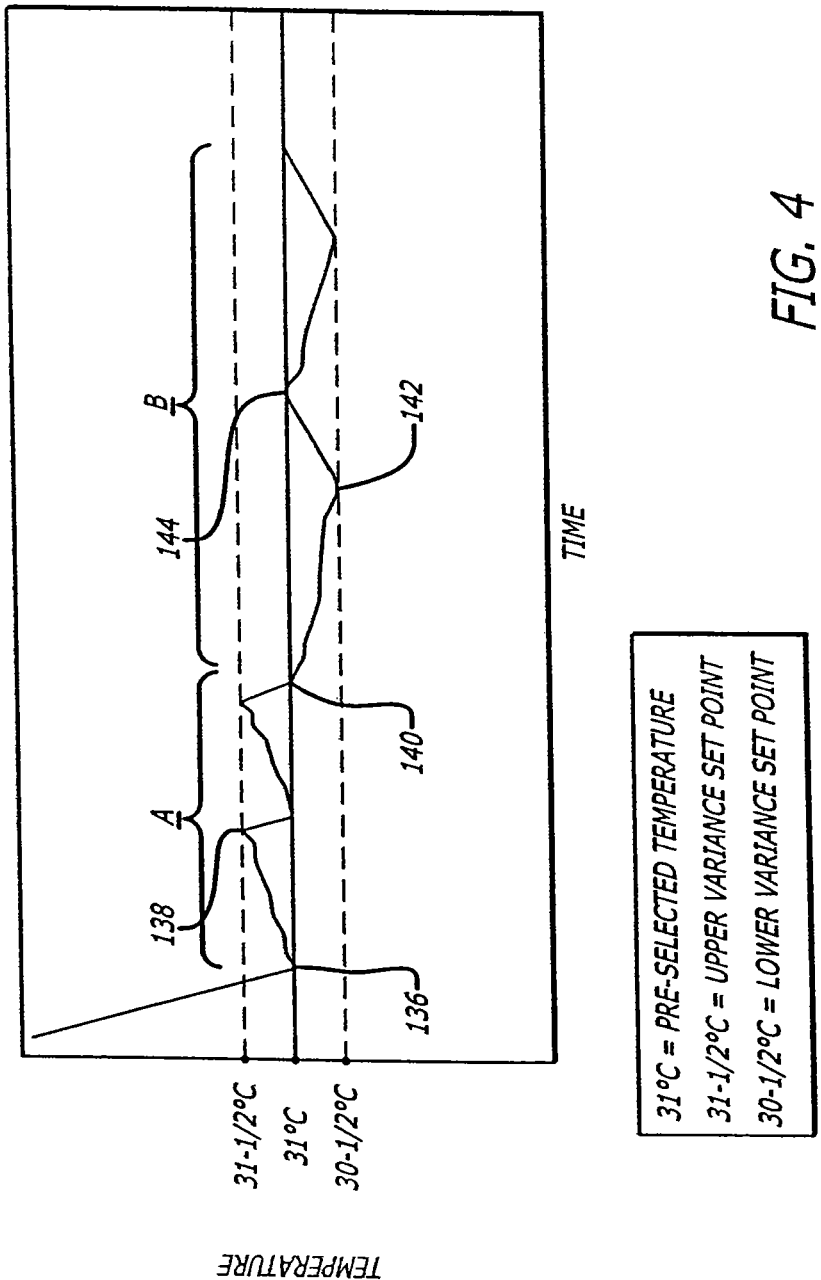
FIG. 4 is a graph of the sensed temperature of a target tissue or body fluid over time under the influence of the control scheme of FIGS. 3A 3B.

FIG. 4 is a graphical illustration plotting the fluctuating sensed tissue temperature over a period of time relative to the target temperature and variance set points using one method of analyzing the sensed temperature data and controlling the heater/cooler to change the temperature of a patient's blood. In the example, the target temperature is set at 31 degrees Celsius, with the upper and lower variance set points ½ degrees on either side. Initially, the sensed tissue temperature is greater than the target temperature, such as if the heat exchange catheter is placed in contact with blood at 37 degrees Celsius. The system is first placed in the COOLING mode so that the sensed tissue temperature is reduced until it equals the target temperature at 136, corresponding to steps 120a and 124 in FIG. 3A. In step 124, the heat exchanger is converted to the OFF mode, which results in the sensed tissue temperature climbing until it reaches the upper variance set point at 138, corresponding to step 130 in FIG. 3B, at which time the system begins cooling again. This cycle is repeated in the region indicated at A.

Eventually, the patient may be unable to maintain even the target temperature as shown by the temperature profile in the region indicated at B. For example, after the sensed tissue temperature reaches the target temperature at 140, and the heat exchanger is turned OFF, the sensed target temperature may continue to drift lower until it reaches the lower variance set point at 142. The controller logic senses this in step 132 of FIG. 3B, and converts the system to the HEATING mode. Subsequently, the sensed tissue temperature climbs to the target temperature at 144, and the system is again turned OFF, corresponding to steps 120b and 128 in FIG. 3B. Alternatively, depending on the patient and the situation, it may be that after the sensed tissue temperature reaches the target temperature and the heat exchanger is turned OFF, the patient's temperature may begin to increase until it rises to the upper variance set point temperature, at which point, as described in box 130, the heat exchanger begins to COOL. As can be appreciated, the sensed tissue temperature continues to fluctuate between the upper and lower variance set points in this manner. As will be discussed in more detail below, other control schemes, such as PID control scheme, may be used to control the heating and cooling of the patient's blood.

The control scheme as applied to the system of the present invention has the advantage of allowing the operator to essentially input a desired temperature after which time the system will automatically regulate the tissue temperature until it reaches the target temperature, and will maintain the tissue temperature at that target temperature.

It should also be understood, in accordance with the present invention, that the controller processor 70 may be configured to simultaneously respond to multiple sensors, or to activate or de activate various components such as several heat exchangers. In this way, for example, a controller might heat blood that is subsequently circulated to the core body in response to a sensed core body temperature that is below the target temperature, and simultaneously activate a second heat exchanger to cool blood that is directed to the brain region in response to a sensed brain temperature that is above the target temperature. It may be that the sensed body temperature is at the target temperature and thus the heat exchanger that is in contact with blood circulating to the body core may be turned off by the controller, while at the same time the controller continues to activate the second heat exchanger to cool blood that is directed to the brain region. Any of the many control schemes that may be anticipated by an operator and programmed into the control unit are contemplated by this invention.

A further advantage of the system of the present invention is that all of the portions of the system that are in contact with the patient are disposable, but substantial and relatively expensive portions of the system are reusable. Thus, the catheter, the flow path for sterile heat exchange fluid, the sterile heat exchange fluid itself, and the pump head are all disposable. Even if a rupture in the heat exchange balloon permits the heat exchange fluid channels and thus the pump head to come in contact with a patient's blood, no cross contamination will occur between patients because all those elements are disposable. The pump driver, the electronic control mechanisms, the thermoelectric cooler, and the manual input unit, however, are all reusable for economy and convenience. Desirably, as illustrated, all of these re usable components are housed within a single control unit 50, although other configurations are possible. Likewise, the various sensors distributed around a patient's body and along the catheter may be disposable, but the controller processor 70 to which they attach is re usable without the need for sterilization.

It will also be appreciated by those of skill in the art that the system described herein may be employed using numerous substitutions, deletions, and alternatives without deviating from the spirit of the invention as claimed below. For example, but not by way of limitation, the serpentine pathway 100 in the heat exchange plate 96 may be a coil or other suitable configuration, or the sensors may sense a wide variety of body locations and other parameters may be provided to the processor 70, such as temperature or pressure. Further, the in dwelling heat exchanger 76 at the end of the catheter 52 may be any appropriate type, such as a thermoelectric heating/cooling unit which would not require the circulation of a heat exchange fluid. If a heat exchange balloon is provided, a pump might be provided that is a screw pump, a gear pump, a diaphragm pump, a peristaltic roller pump, or any other suitable means for pumping the heat exchange fluid. All of these and other substitutions obvious to those of skill in the art are contemplated by this invention.

Exemplary Heat Exchange Catheter Control Unit

FIGS. 10A 10C are illustrated views of an exemplary heat exchange catheter control unit 150 of the present invention that is particularly suited for rapid temperature regulation of a patient. The control unit 150 comprises a vertically oriented outer housing having a lower portion 152 and upper portion 154 separated at a generally horizontal dividing line 156 located close to the top of the unit. The lower portion 152 is mounted on wheels 158 for ease of portability, with the wheels preferably being of the swivel type having foot actuated locks. For ease of servicing, the upper and lower portions may be joined together with hinges (not shown) at the back so that the top portion may be lifted up and rotated back to expose the interior of the unit. In an exemplary embodiment, the control unit 150 has a height that enables an operator to easily access an upper control panel 160 without significant bending over. For example, the control unit 150 may have a total height of between approximately 2 3 feet, and preferably about 32 inches. The substantially horizontal cross section of a majority of the control unit 150 may have widths of between one and two feet, although the lower portion 152 preferably widens at its lower end with the wheels 158 mounted on the lower corners to provide greater stability.

FIG. 10A illustrates the assembled control unit 150, while FIGS. 10B and 10C show an exploded view and a subassembly of the control unit. FIG. 10A illustrates the front and right sides of the unit 150 wherein the control panel 160 is visible on an angled upper panel 162 of the upper portion 154 front side. The angled upper panel 162 also defines a fluid container receiving cavity 164 adjacent the control panel 160. Further, a plurality of handles 166 may be provided to help maneuver the control unit 150.

A heat exchange cassette receiving opening 168 is also provided on a front panel 169 of the control unit 150, just below the horizontal dividing line 156. As will be explained below, the opening 168 is sized and shaped to receive a heat exchange cassette of the present invention, analogous to the heat exchange cassette receiving opening 102 shown in FIG. 2. Likewise, the control unit 150 provides all of the features that were described above for the control unit 50 of FIG. 2, including a heater/cooler, a pump driver, a controller processor, and a manual input unit, namely the control panel 160.

Exemplary Control Panel

FIGS. 10B and 10C illustrate in greater detail the upper portion 154 of the control unit 150, and in particular the control panel 160. FIG. 10B shows a facade 172 exploded from the control panel 160, with the facade shown in FIG. 10C having labels printed thereon corresponding to various displays and buttons. (The reader will notice that the control panel 160 in FIG. 10C is an alternative embodiment from the one shown in the rest of the drawings, and includes several added features and with several buttons and/or displays being slightly relocated). The following is a description of the physical characteristics of the control panel 160, with a description of an exemplary method of using the control panel to follow later in the description.

The exemplary control panel 160 of FIG. 10C provides a number of visual displays, including, from top to bottom along the centerline, a patient temperature display 174, a target temperature display 176, a cooling/warming rate display 178, and a system feedback/status display 180. Other desirable information may be displayed, either with an additional display, or alternating with information displayed on one of the screens shown here, or by user initiated request from one of the screens shown here. For example, by way of illustration but not limitation, if the ramp rate for heating or cooling the patient is set by the user, or is calculated by the control microprocessor, or the projected time to target temperature is calculated, those values may be shown.

The larger displays for alphanumeric characters are preferably liquid crystal displays (LCD), while several light emitting diode (LED) status indicators are also provided. Several graphic icons are positioned adjacent the left of the upper three LCD displays 174,176, and 178, to indicate their respective display functions.

Specifically, a patient temperature icon 182*a*, a target temperature LED 182*b*, and a cooling/warming rate LED 182*c* are provided. Just below the cooling/warming rate LED 182*c*, an operational mode LED 182*d* and associated vertical series of three mode indicators 184 are provided. Only one of the indicators 184 lights up at any one time, depending on whether the system is in the COOLING, WARMING, or MAINTAINING mode.

In lieu of the mode indicators 184, the display 180 may carry the message COOLING PATIENT, WARMING PATIENT, or MAINTAINING so that the operator can easily identify the mode of functioning of the controller. There also may be only one patient temperature icon 182 which has a line of lights that streams upward if the unit is warming, downward if the unit is cooling, and blinks stationary if the unit is maintaining. Finally, a power on/off indicator LED is provided in the lower left corner of the control panel 160.

The control panel 160 also exhibits a number of input buttons including, in descending order on the right side of the control panel, a Celsius/Fahrenheit display toggle 190, a pair of target temperature adjustment buttons 192, a pair of cooling/warming rate adjustment buttons 194, a multi function/enter button 196, and a mute audible alarm button 198. The mute audible alarm button 198 is nested within an LED alarm indicator 200. Finally, in the lower central portion of the control panel 160, a stop system operation button 202 permits instant shutdown of the system.

Control Unit Housing

The control unit housing, described herein but not shown in detail, is defined by a number of panels, some of which can be removed to view and access the interior contents of the control unit 150. A subhousing encloses a relatively large blower fan (not shown) that interacts with a thermoelectric cooler/heater, and is separated therewith by a first filter (not shown) spanning a circular upper opening and held thereon by a gasket. A second air filter covers a square opening in the bottom of the subhousing within the control unit such that air blown (upward or downward) through the circular opening is double filtered. Finally, a drain cup may be provided in the bottom of the control unit 150.

Heat Exchange Cassette Receiving Subassembly

The following discussion of the heat exchange cassette receiving subassembly (not shown) is provided for a general review and is not illustrated in detail. The subassembly comprises, from top to bottom, an upper pressure plate, a pair of elongated side spacers, an upper guide assembly, a lower guide assembly, a pump drive mechanism attached to and depending downward from the lower guide assembly, a rear water channel assembly, a heater/cooler subsystem, and an air cooler disposed directly below the heater/cooler subsystem. In addition, a fluid level measurement sensor module is adapted to be mounted to the underside of the lower guide assembly.

The air cooler comprises a hollow box like structure having solid front and rear walls, a circular opening in the bottom wall to communicate with the interior of the tubular skirt, and a pair of side walls with vents that register with the vents in the surrounding control unit housing. In addition, the air cooler is exposed to the underside of the heater/cooler subsystem. This is accomplished by fastening a portion of the heater/cooler subsystem over the open topped box of the air cooler. In this manner, air blown through the tubular skirt (either upward or downward) flows past the underside of the heater/cooler subsystem. If the air is blown upward, it is redirected sideways through the vents and to the external environment. If the air is blown downward, it is pulled in through the vents and is redirected downward through the first filter in the circular upper opening, and out through the second air filter covering the square opening to the external environment. The air cooler therefore acts as a highly efficient convective heat sink for the heater/cooler subsystem.

The heater/cooler subsystem houses a plurality of thermoelectric (TE) modules (not shown). The TE modules are preferably discrete modules distributed over the surface of a lower plate. In the exemplary embodiment, there are twelve square TE modules distributed in rows and columns across substantially the entire area of the lower plate. The TE modules preferably function on the well known Peltier principal, wherein the same TE modules may either heat or cool depending on the direction of DC current through the units. All the TE modules described here are arranged so that current flows through each in the same direction. Therefore, merely by changing the polarity of the current flowing through the TE module the heater/cooler subsystem can be instantly changed from a heater to a cooler or visa versa. The amount of heat or cold generated can also be adjusted by controlling the amount of current flowing through the TE modules. Thus a very high level of control may be exercised by control of only one variable, the DC current supplied to the TE modules.

The upper plate provides a conductive heat transfer interface between TE modules and the heat exchange cassette inserted within the cavity, and tends to distribute the discrete temperature differentials provided by the TE modules over its surface. This helps to prevent localized heating or cooling of the heat exchange cassette, which may provoke an erroneous temperature measurement. Further, the upper plate is manufactured of a suitably rigid metal having good thermal conductivity, such as anodized aluminum or other suitable material. The various components of the subassembly creates an internal cavity into which a heat exchange cassette of the present invention can be inserted.

The heat exchange cassette receiving subassembly further includes a system for driving a pump provided in the heat exchange cassette. More specifically, the pump drive mechanism (not shown) is attached to the underside of the lower guide assembly for powering a pump in the heat exchange cassette. The pump drive mechanism preferably includes an electric motor attached to the underside of the lower guide assembly and having an output shaft (not shown) engaged with a drive belt that, in turn, rotates a pump drive shaft via a pulley, the drive shaft being journaled to rotate within a vertical through bore in the lower guide assembly. Other alternative methods of transferring rotational motion from the pump drive motor are clearly anticipated by this disclosure and may include a series of gears between the electric motor and the output shaft, a direct drive mechanism whereby the electric motor directly engages the pump in the cassette, or other similar configurations.

Electronic Control Circuit

As an alternative to the control system described in conjunction with FIGS. 3A 3B and the graph of FIG. 4, the controller may employ a cascading PID control scheme. In such a scheme, a control board is provided that may be divided into two sections: (a) a Bulk PID control section which takes input from the user (in the embodiment shown, RAMP RATE and TARGET TEMPERATURE) and input from the sensors on the patient representing patient temperature, and calculates an intermediate set point temperature (SP1) and an output signal to the Working Fluid PID control; and (b) the Working Fluid PID control, that receives input from the Bulk PID control section and from a sensor representing the temperature of the heat exchange fluid, and generates a signal that controls the temperature of the TE cooler by varying the power input to the TE cooler.

In various embodiments of the present invention, which will be discussed in more detail below, the working Fluid PID control may also generate control signals to slow or stop the pump motor or divert the heat exchange fluid to by pass the heat exchange catheter. Alternatively, a Fluid Diverter PID controller may initiate fluid diversion from the heat exchange catheter. The heat exchange fluid circulates in heat transfer proximity to the TE cooler, so the Working Fluid PID essentially controls the temperature of the working fluid. In this way, the control scheme is able to automatically achieve a specified target temperature at a specified RAMP RATE based on input from sensors placed on the patient and the logic built into the controller. Additionally, this scheme allows the unit to automatically alter the patient temperature very gradually the last few tenths of a degree to achieve the target temperature very gently and avoid overshoot or dramatic and potentially damaging swings in the electronic power to the TE cooler. Once the target temperature is achieved, the system continues to operate automatically to add or remove heat at precisely the rate necessary to maintain the patient at the target temperature.

Figure 10:
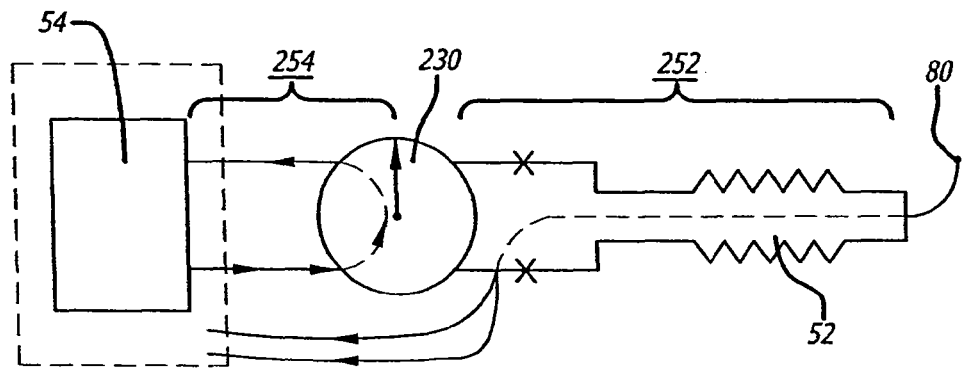
FIG. 10 is a side view of the diverter of FIG. 9 but with the diverter valve in a diversion orientation.
Figure 11:
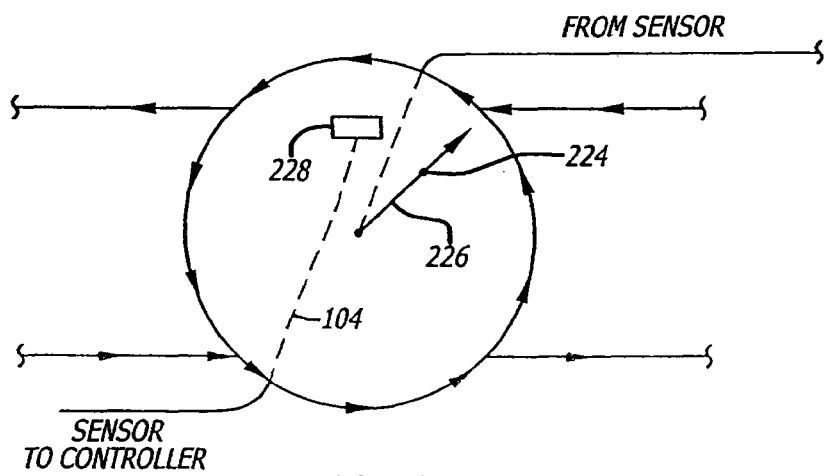
FIG. 11 is a side view of an embodiment of a diverter flow valve having a rotary arm and sensor for periodically interrupting the flow of fluid from a catheter depicted in full flow mode.

FIG. 11 illustrates an exemplary electronic control circuit of the present invention specifically adapted for use in control unit 150 of FIG. 10A, but applicable to any control unit described herein. Some of these elements correspond to elements identified previously, and thus, where appropriate, reference numbers will be repeated for clarity. In general, the control circuit includes a control board having a number of logical components indicated within the dashed line 322, a user input 324, a display output 326, a plurality of sensors 328, a number of elements of electronic hardware indicated within the box 330, and a safety system 332. The user inputs 324 and display outputs 326 were described above with respect to the control panel 160 of FIG. 10C. The two user inputs 324 applicable to the control circuit in this embodiment are the target temperature adjustment buttons 192 and cooling/warming rate adjustment buttons 194. The display outputs 326 applicable to the control circuit are the patient temperature display 174 and the alarm display 200, but may include a number of other displays for various feedback to the user. A plurality of sensors 328 may be provided, including at least a sensor 327 that senses the patient's actual body temperature and generates a signal represented by line 326, and a sensor 329 that senses the temperature of the working fluid and generates a representative signal 331. As stated previously, the working fluid may be, for example, saline that is heated or cooled by passing in heat exchange proximity with a TE cooler 348 and then is circulated within a heat exchange catheter.

After the system is primed, a set point temperature (SP1) is determined with a set point calculator 334 using the target temperature and the desire ramp rate as inputs. This set point temperature represents an interim target temperature that the system will achieve at any given time, for example 0.1° C. each 6 minutes, if the ramp rate is 1° C. per hour, starting with the initial patient temperature. This set point temperature is transmitted to a Bulk PID control section 336 of the control board. The Bulk PID control 336 also receives input from the body temperature sensor 327.

Based on the differential between the SP1 and actual body temperature, if any, the Bulk PID control 336 raises or lowers the temperature specified for the heat exchange fluid that will be circulated through the exchange catheter so as to induce a change to the patient temperature at the specified ramp rate. That is, a value for the desired working fluid temperature, or a second set point temperature (SP2), is transmitted to a Working Fluid PID control unit 338 as illustrated at 337. The Working Fluid PID control unit 338 also receives input from the temperature sensor 329 for the working fluid as illustrated at 333. The Working Fluid PID control unit 338 compares the sensed working fluid temperature with the desired working fluid temperature transmitted from the Bulk PID control to determine a differential, if any. Based on this differential, the Working Fluid PID control 338 transmits a digital signal as illustrated at 340 to an "H Bridge" polarity switching unit 342, which directs power of an appropriate magnitude and polarity to the TE cooler 348 to cause the TE cooler to be heated or cooled toward the desired temperature. This, in turn, heats or cools the working fluid as the system operates to circulate the working fluid in heat exchange proximity to the TE cooler.

The polarity switching unit 342 receives power from a source 344 and transforms that power to the appropriate magnitude and polarity requested by the Working Fluid PID control unit. Between the power source and the polarity switching unit is a safety relay 346 actuated by the safety system 332 that will, in the absence of a safety issue, transmit the power from the power source 344 to the polarity switching unit 342. If the safety system 332 is aware of a safety issue, for example if a low fluid level is sensed, it may direct the safety relay 346 to open and prevent power from the power supply 344 from being directed to the TE cooler 348. In the absence of any safety issue, however, the polarity switching unit 342 transmits the power to the heater/cooler unit 348 in accordance with the request from the Working Fluid PID control unit. Various subsystems of the present invention provide input to the safety system 332, and will be described below when introduced.

The control circuit includes logic that permits rapid heat exchange when the target temperature and the sensed body temperature are relatively far apart, and which slows down the rate of heat exchange as the sensed body temperature nears the target temperature. As the sensed patient temperature and the SP1 become very close, the Bulk PID will dictate only a very small change in the working fluid temperature, and thus the rate of change will become smaller and smaller as the SP1 becomes very close to the sensed patient temperature until the rate of change is essentially non existent. In this way, the patient temperature very gently is heated or cooled the last few tenths of a degree, avoiding overshoot or dramatic swings from heating to cooling when the body temperature is at the target temperature. As the input TARGET TEMPERATURE is reached, the SP1 and the TARGET TEMPERATURE are essentially the same, and the system operates to set the power to the TE cooler at a level that maintains the necessary working fluid temperature to hold the patient temperature at the TARGET TEMPERATURE. In this way, the system will work to maintain a target temperature with the working fluid maintained at just the right temperature to add or remove heat at the precise rate necessary to maintain that target temperature as essentially a steady state.

The Working Fluid PID control 338 samples its respective inputs at a rate of 10 times a second and updates the output to the polarity switching unit 342 at a rate of once every second, and thus the trends of changing patient temperature are constantly monitored and adjusted. The Bulk PID control 336 samples its inputs at the same rate, and thus a new target temperature or a new ramp rate can be specified by the user with nearly instantaneous system response.

Exemplary Method of Fluid Control and Temperature Measurement

Various methods have been used in attempts to maximize the accuracy of measuring the temperature of the target tissue of a patient in order to accurately control the heating or cooling of the tissue, and to prevent under- or over-shoot. Most prior attempts required that the temperature be measured using an esophageal temperature probe, or by using temperature probes placed in various blood vessels of a patient's body. Such schemes, however, are difficult to employ and typically require that multiple "sticks" be made in a patient. Because each "stick" requires another puncture of the patient, they provide multiple opportunities for infection or other adverse side effect. Moreover, multiple "sticks" may result in use of major vessels for temperature measure that may also be needed for a supplemental or different treatment, thus making those vessels unavailable for use.

For these reasons, attempts have been made to include a temperature sensor in the heat exchanger in the vessel, or mounted externally of the heat exchanger. The disadvantage of only measuring the temperature of fluid within the heat exchanger in the vessel is that the sensor is not in direct communication with the blood flowing past the heat exchanger and thus does not measure the temperature of the blood. Such an arrangement requires that the flow of heat exchange fluid be stopped periodically to allow the temperature of the heat exchange fluid within the heat exchanger to come to equilibrium with the temperature of the blood outside of the exchange exchanger. This wait can be time consuming, requiring a longer time to reach the desired final target temperature. Moreover, every time the pump is turned off, the natural heat generation of the patient's body causes the body temperature to rise when being cooled, adding to the thermal energy that must be removed from the patient's body, and thus the time to reach the desired target temperature.

Mounting the sensor on the shaft of the catheter so that it measures blood temperature also entails difficulties in determining an accurate blood temperature. The sensors used currently, typically thermistors, are very fast and sensitive devices. The nature of blood flow due to incomplete mixing, swirling and other factors results in small fluctuations in flow as blood flows past the heat exchanger. These fluctuations in flow, particularly those resulting from incomplete mixing of the heated or cooled blood flowing adjacent the heat exchanger with blood flowing a further distance away from the outside wall of the heat exchanger, may be sensed by the thermistors as changes in temperature. This fluctuating temperature signal renders an accurate determination of the true temperature of the blood downstream of the heat exchanger difficult to achieve. An example of the temperature signal fluctuation can be seen in the graph of FIG. 16.

One method of obtaining an accurate measure of a patient's core body temperature using a temperature sensor located in the patient's blood stream distal of the heat exchanger can be achieved by stopping the flow of heat exchange fluid and monitoring the temperature of the blood downstream of the heat exchange catheter during the stoppage of flow. This result may be achieved by slowing or stopping the fluid pump motor and waiting for a period of time until a clear temperature signal is achieved. Alternatively, the same effect can be accomplished by diverting the flow of heat exchange fluid into a circuit that does not circulate the fluid through the heat exchange catheter. It will be understood that the same applies to the situation where the heat exchanger is located in a vessel such that blood from the distal portion of the heat exchange catheter flows towards the proximal portion of the catheter. In this case, the temperature sensor may be mounted proximally to the heat exchanger.

Figure 15:
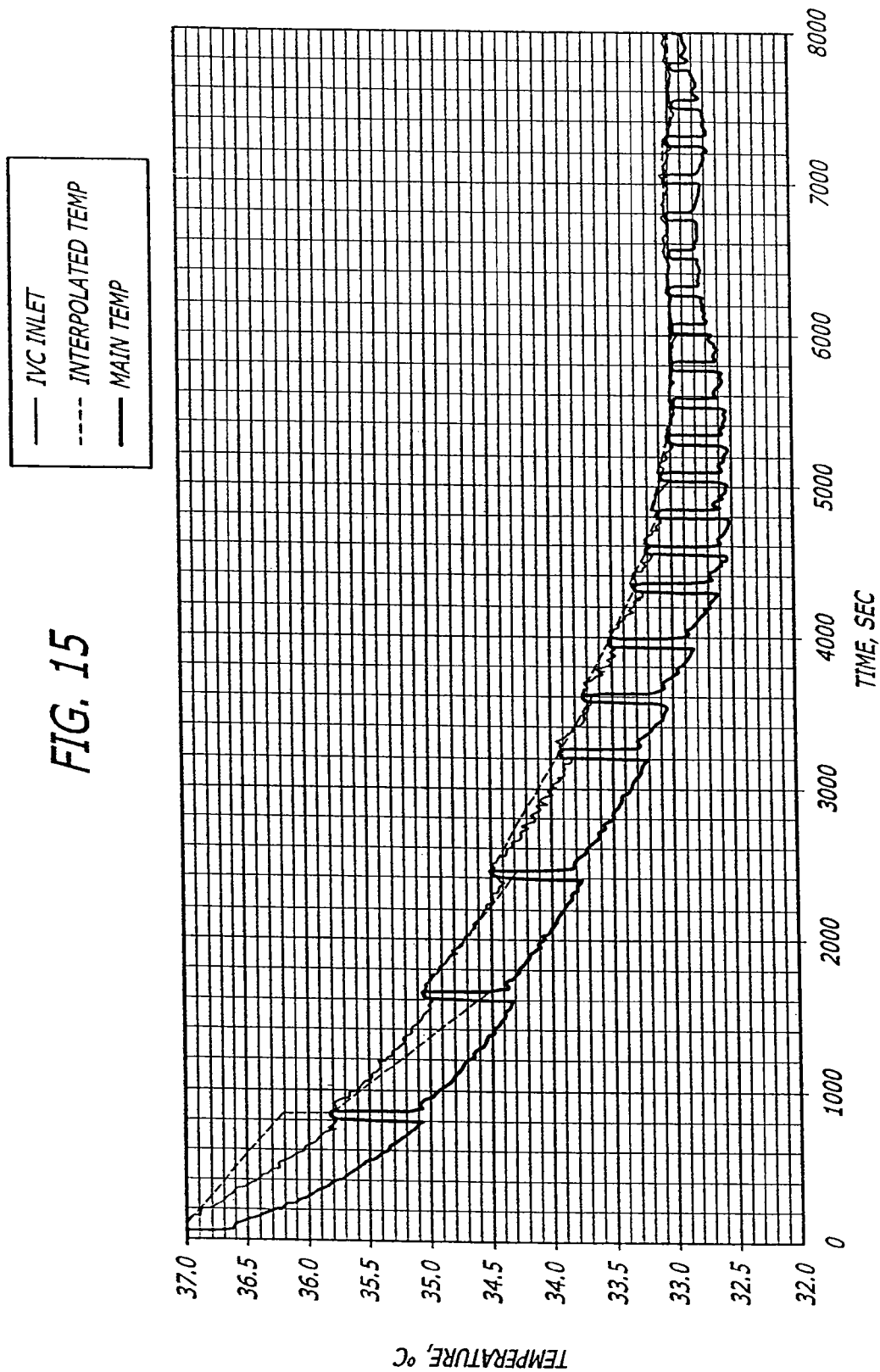
FIG. 15 is a graphical presentation of temperature data accumulated using an embodiment of the present invention to controllably cool a volume of fluid during a bench test.

The graph of FIG. 15 depicts one embodiment of the present invention where the pump was stopped for a period of time and the temperature of the blood distal to the heat exchanger was monitored for a selected period of time. The data of FIG. 15 was obtained by measuring the temperature as a function of time of a fluid reservoir of a known volume in which had been placed a heat exchanger in accordance with the present invention. In the laboratory model, a temperature sensor was placed at a location distal of the heat exchanger. This temperature is a representation of the actual temperature of the fluid flowing past the heat exchanger.

The line identified as "Main Temp" is a recording of the temperature measured by a sensor located distal of the heat exchanger, such as that of sensor 80 (FIG. 2). At each time period, the difference in the measured temperatures of the IVC inlet and Main Temp values is due to the cold fluid flowing through the heat exchanger. Using mathematical methods well known in the art, such as described below in the equation below, an interpolated temperature may be calculated, such as that shown in FIG. 15. As is readily observable, stopping the flow of fluid through the heat exchanger results in the Main Temp increasing until it approximates the IVC inlet temperature, and also allows the interpolated temperature to be calculated to more closely approximate the IVC inlet temperature. The fluid flow stoppage may be prolonged for a selected period of time, or a predictive algorithm may be used to analyze the change in measured temperature over time as it approaches the actual temperature, and to determine the optimal time flow may be stopped and still be able to predict the point that the Main Temp will approximate the actual temperature of the blood.

Various methods may be used to interpolate patient temperature based on the temperature measured during pump stoppages. For example, linear interpolation based on the equation:

$$y = mx + b$$

may be used. Alternatively, other interpolation or trending methods, such as exponential, logarithmic or polynomial based methods, may also be used.

Substituting appropriate variables into the above equation yields:

$$T(t) = R_t * t * D + T_0$$

where:
T=Temperature
$T_0$=Last known temperature
t=Time
T(t)=Temperature as a function of time
$R_t$=Rate of temperature change
D=Decay factor.

The method of this embodiment utilizes two know temperatures and calculates the rate of temperature change between the last two known temperatures, and then uses the calculated rate to estimate the patient's temperature at a future time. When the pump is stopped, either due to a predetermined time interval, a change in pump speed, or because the patient's temperature is approaching a target temperature, or has reached a predetermined temperature at which it is desired to measure the patient's actual temperature, the system determines the current patient temperature and recalculates a new temperature rate. Since the heat transfer between the blood and heat exchanger diminishes as the difference between the blood temperature and heat exchange fluid temperature decreases, each projected rate of temperature change is expected to be less than the previous rate of change. Thus, a decay factor may be used to adjust the calculated rate used to project future patient temperature. The decay factor may be, for example, a constant value or it may be dependent on the difference between patient temperature and target temperature, fluid temperature, the difference between heat exchange fluid temperature and patient temperature, or other like factors.

Example 1

A catheter that has a temperature probe mounted on the catheter tip is placed inside a patient. Prior to starting therapy, that is, when the system is not yet cooling, the temperature probe measures 37.00° C. The cooling process is then started with a target temperature of 33.0° C. Since the system has only determined a starting temperature and cannot yet determine a rate of cooling, the system can, for example, use an expected rate of cooling to estimate the patient temperature. In this example, an expected rate of cooling of −5 degrees per hour, or −1.3889×10-3 degrees per second is desired. Therefore, using the equation set forth above, the estimated patient temperature is calculated as follows and updated, for the purposes of this example, but not intended to be limited thereto, once per second. Thus:

$$T(t) = (-1.3889 * 10^{-3}) * (t) * (1.0) + 37.00 \text{ where } D = 1.0$$

Using this calculation, after 600 seconds, the estimated temperature would be 36.17. At this point (t=600 seconds), the controller may be preprogrammed to pause the pump and wait for the probe temperature to equilibrate. Once it has determined the current patient temperature, 36.00° C. in this example, the controller restarts the pump and the system estimates patient temperature based on a new rate. In this case, the new rate would be equal to:

$$R_t = \frac{T(t_i) - T_0}{t_i - t_0} \text{ or}$$

$$R_t = \frac{36.00 - 37.00}{600 - 0} = -1.6667 * 10^{-3} \text{ degrees per second.}$$

At any time between the most recent pump stoppage (at t=600) and the next pump stoppage, the estimated patient temperature would be calculated as:

$$T(t) = (-1.6667 * 10^{-3}) * (t - 600) * (1.0) + 36.00$$

For example, the estimated patient temperature after 800 seconds would be calculated as:

$$T(t=800) = (-1.6667 * 10^{-3}) * (800 - 600) * (1.0) + 36.00 = 35.67° C.$$

One advantage of using the embodiment of the method of the present invention set forth above is that the temperature sensor may be placed on or inside the catheter shaft or heat exchanger, inside a guide wire lumen of the catheter, at or close to the tip of the catheter, or at a location distal or proximal to the catheter tip or heat exchanger. Another advantage is that the method of this embodiment of the present invention allows use of a PID controller, since this method provides continuous feedback to the control system. However, location of the temperature sensor will affect the length of time required to stop the flow of heat exchange fluid through the heat exchanger, and each stoppage or slowing of the pumping of heat exchange fluid through the heat exchanger decreases the maximum achievable cooling or warming rates of the system.

As described previously, the fluid flow stoppage through the heat exchanger may be effected by either stopping the pump, or alternatively, reducing the fluid flow through the heat exchanger sufficiently so that the rise in sensed temperature can be analyzed to determine when it will approximate the actual temperature of the blood. Thus, it is not necessary to completely stop the pump, which may be advantageous where inertia or friction within the pumping mechanism are a concern.

Alternatively, the flow to the heat exchanger may be diverted from the heat exchanger and back through the heating/cooling circuit without stopping the pump. One embodiment of such a diverter 210 is illustrated in FIGS. 5 through 7A. A cassette 54 containing heat exchange fluid and having a pump head is installed into a controller 50 having a pump motor for activating the pump head to direct heat exchange fluid out the output channel 62b and then through inflow lines toward a heat exchange region 250 of catheter located in a patient's bloodstream. While the following description discusses the operation of the diverter 210 with respect to cooling a patient's body temperature, those skilled in the art will understand that the same principles and methods are equally applicable to warming a patient, or maintaining a patient at a selected temperature.

When operating to cool a patient by cooling the heat exchange region, the heat exchange fluid circulates through the cassette which is in thermal contact with a thermal electric cooler 66. The fluid is cooled in the controller, directed out through the output channel 62b, through the diverter 210, then through the inflow line 62a. The fluid circulates through the heat exchange region 250, back through the outflow line 62b and through the diverter 210 into the cassette through the cassette inflow channel 62a.

A temperature sensor 80 is inserted in the blood stream, for example, by placement through a central working lumen of the heat exchange catheter, or, as described above, integrated into the catheter and located distal of the heat exchanger. As previously described, the probe may have a thermistor, or two or more thermistors for redundancy, disposed on the distal portion of the probe for sensing the temperature of the blood after it has flowed past the heat exchanger. The thermistor or thermistors generate one or more signals representing the temperature sensed by the thermistors, which are communicated to the controller 70 by suitable electrical connectors 60. Alternatively, the signals from the temperature sensors may be communicated to controller 70 using a wireless means using suitable hardware associated with the sensors and the controller respectively, such as infrared, RF, or other wireless communication methods and protocols known in the art.

The exemplary diverter 210 depicted in FIGS. 5-7A includes a solenoid activated diverter valve 212 located between the output/input channels 62a, 62b and the inflow/outflow lines 88, 92. When the valve 212 is in the diverting orientation (FIG. 6, 7A), it diverts flow directly (indicated by the arrows) from the output to the input channel, circumventing the inflow/outflow lines and heat exchange catheter altogether, circulating the fluid within the cassette. This has the effect of stopping the flow of cooled heat exchange fluid in the catheter, allowing a more accurate measurement or estimation of the temperature of the blood, as described above.

When the controller determines that an appropriate interval has passed, based on an analysis of the temperature signal received from sensor 80, it communicates a signal to the diverter 210 to open valve 212 (FIGS. 5-7) and allow the heat exchange fluid to flow through the catheter to the heat exchanger to again cool the patient.

Figure 7:
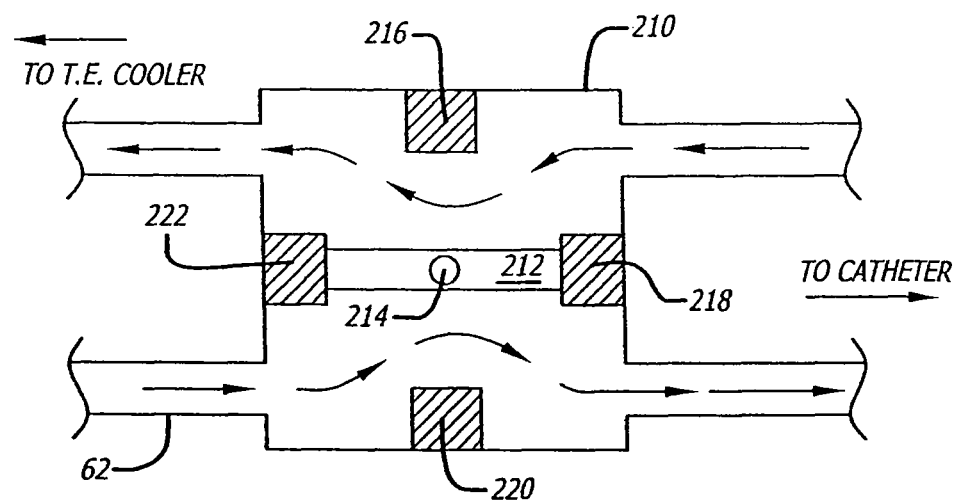
FIG. 7, 7A is a plan view of an embodiment of the diverter unit depicted in the full circuit position allowing heat exchange fluid to pass through the diverter and into the heat exchange circulation circuit.
Figure 7A:
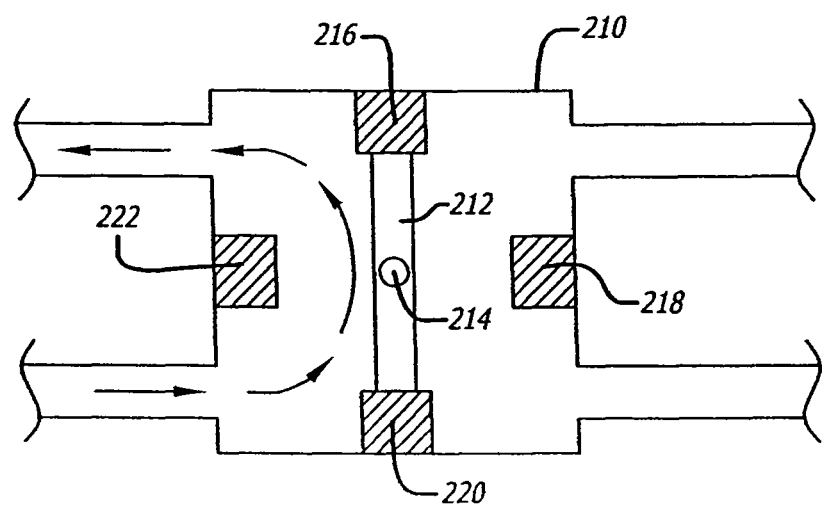
Figure 8:
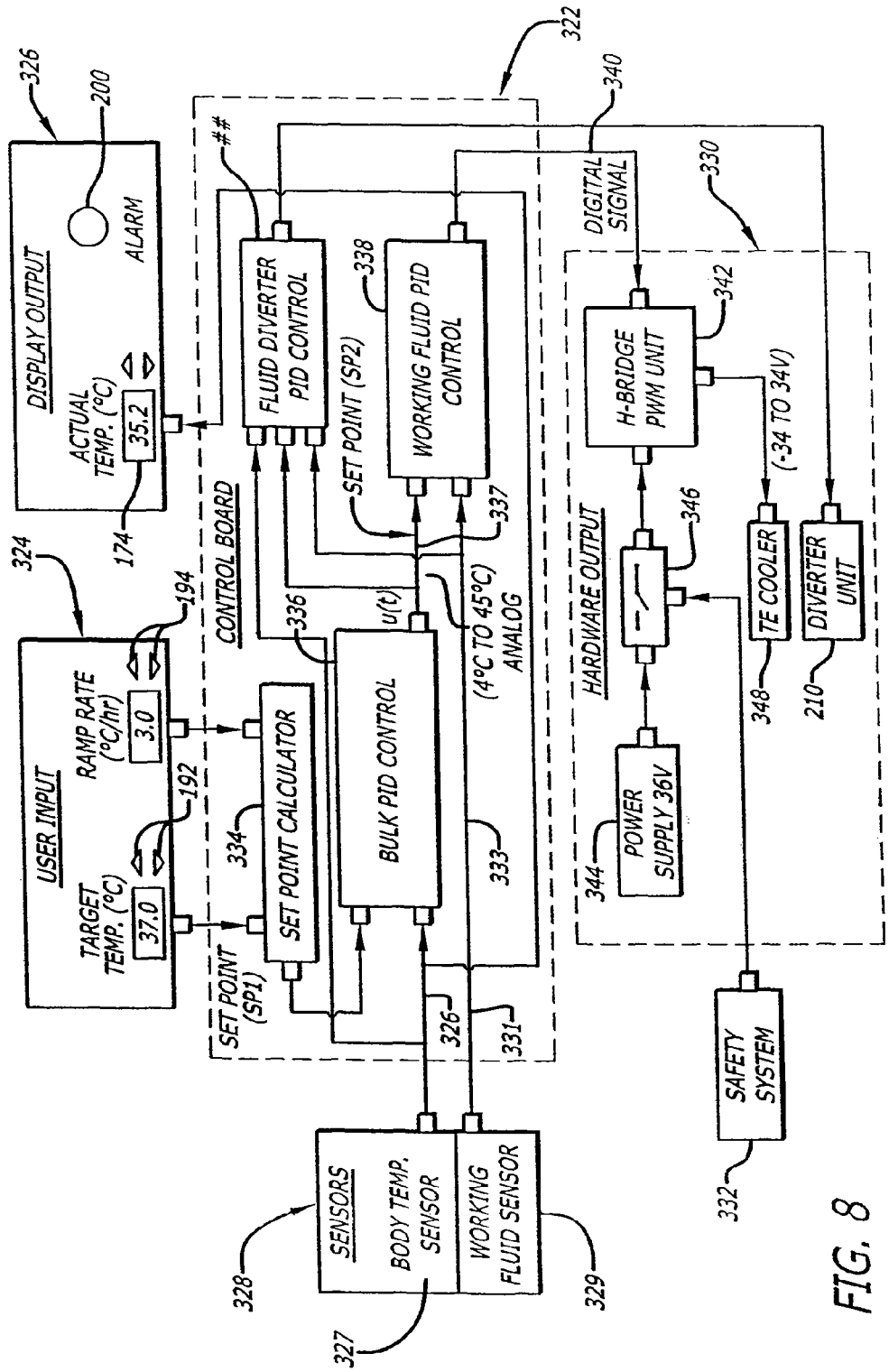
FIG. 8 is a schematic diagram of an embodiment of a control circuit of the present invention including circuitry for controlling a diverter.

A schematic representation of one embodiment of diverter valve in accordance with the present invention is illustrated in FIGS. 7 and 7A. A diverter vane 212 is movable between a diversion orientation (FIG. 7A) and a flow-through orientation (FIG. 7) in response to a signal from the controller. In this illustration, the diverter 210 is depicted as a vane 212 rotating on a shaft 214 to seal with sealing blocks 216, 218, 220, 222, to alter the flow path. Alternatively, the vane may seal directly with the diverter wall, and no sealing blocks would be required.

The diverter valve may be any acceptable diverter valve that can be activated by the controller. There is no requirement that the diverter 210 be a separate component connected to the cassette by fluid conduits, and, in one alternative embodiment, the diverter 210 may be located within the cassette itself. If the diverter valve is in the cassette, for example, positioned directly at the pump outlet, the heat exchange fluid may circulate directly from the pump outlet back to the cassette inlet and thus avoid circulation through the output/input channels.

Figure 12:
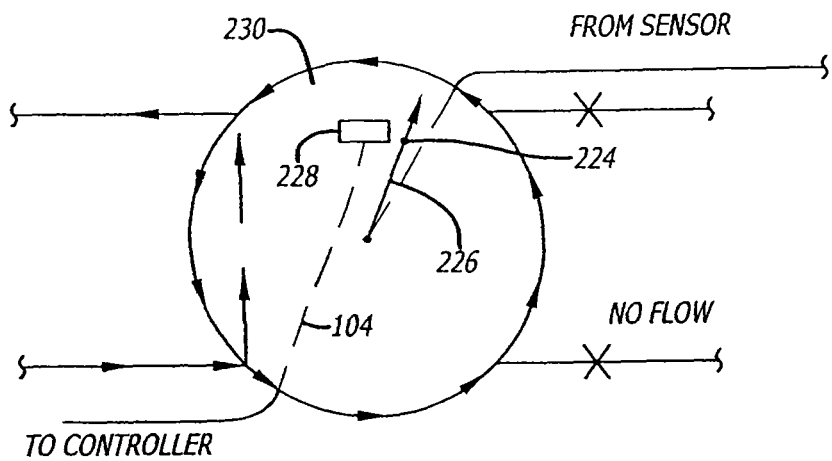
FIG. 12 is a side view of the diverter flow valve of FIG. 11 depicted diverting flow the flow of fluid away from the catheter, but before the rotary arm activates a sensor to provide a signal to a controller.
Figure 13:
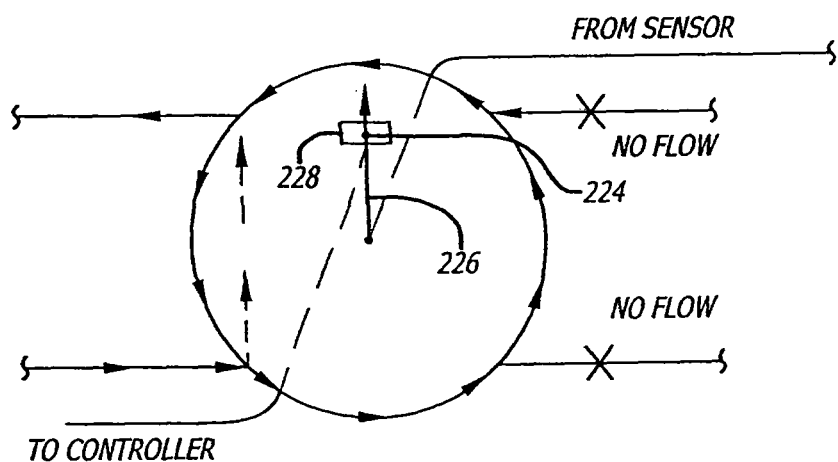
FIG. 13 is a side view of the diverter flow valve of FIG. 11 depicted diverting the flow of fluid away from the catheter, and where the rotary arm is activating the sensor to provide a signal to the controller.
Figure 14:
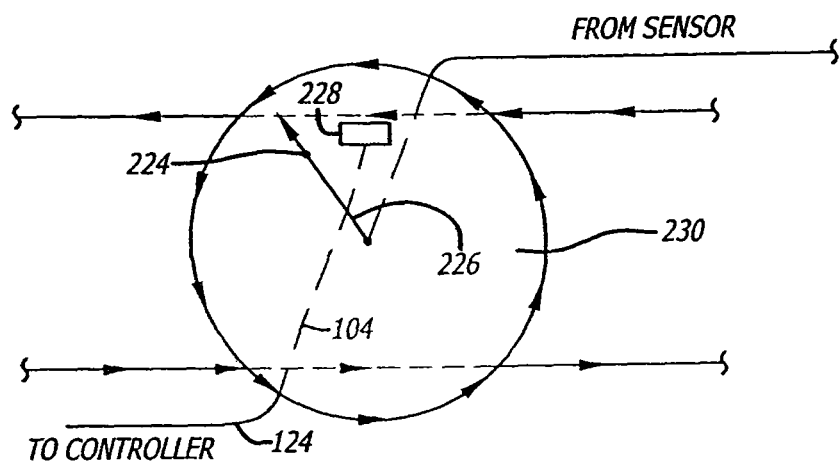
FIG. 14 is a side view of diverter flow valve of FIG. 11 depicted having the rotary arm passed the sensor and restoration of the full flow mode.

FIGS. 12-14 depict another embodiment of a diverter according to the present invention that includes a recycle valve 230 in the fluid flow path to periodically short circuit the fluid flow from the catheter portion of the circuit 252 so that it flows only through the cassette circuit 254 and is diverted away from the heat exchange catheter 52. FIG. 12 depicts the full circuit of fluid flow, where heat exchange fluid is cooled/warmed in the cassette 54, and circulated through the heat exchange catheter 52, and then back through the cassette in a full circuit path. FIG. 13 depicts the same circuit as FIG. 12, but the valve 230 is in the diversion orientation so that the fluid flows in a closed circuit from the cassette, to the valve, and directly back to the cassette, and is thereby diverted from circulating through the heat exchange catheter.

If the heat exchange fluid is not flowing through the catheter, the temperature sensed by a temperature sensor 80, even if the sensor is very near the catheter, accurately reflects the temperature of the blood. If the cold/warm heat exchange fluid is circulating through the heat exchange catheter, then the temperature sensed by a temperature sensor 80 near the heat exchange catheter 52 is unacceptably influenced by the temperature of the heat exchange fluid, unless the temperature sensor is located sufficiently far from the heat exchanger. The fluid flow through the catheter need only be interrupted for a short time, for example 15 seconds, for the second temperature to be an accurate temperature for the blood or the core patient temperature.

Although it is well known in the art that the temperature inside a catheter and its external environment may typically differ by 10-40° C. during operation, due to the presence of cold or warm heat transfer fluid within the catheter, current methods of temperature control follow the belief that interrupting controlled temperature regulation may tend to reduce the accuracy of the temperature of the controller, therefore requiring the need for predictive algorithms that avoid waiting for complete equilibrium temperature. However, the preferred method of the present invention requires periodic temperature sampling only after the cooled/heated exchange fluid has ceased circulation and achieved temperature equilibrium.

Figure 9:
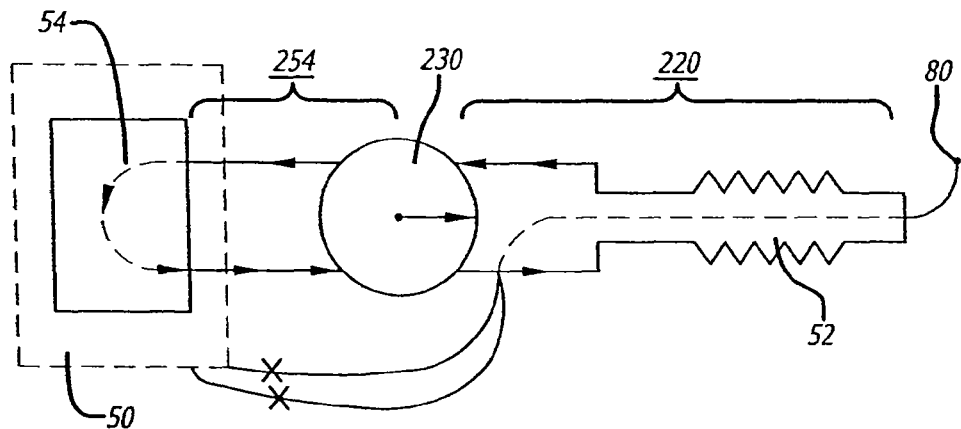
FIG. 9 is side view of the flow valve system having the diverter valve in a full circuit orientation.

A flow actuated valve 230, i.e. a valve that constantly rotates from a full circulating orientation, as shown in FIG. 9, to a short circuiting orientation, FIG. 10, may be placed into the exchange fluid flow stream. An electrical contact 224 may also be attached to a rotating member 226 on the valve 230. A signal is received from the sensor 80 to the rotating member 224. An electrical contact pad 228 has an electrical conductor 104 leading to the controller 50. Initially, as depicted in FIG. 11, the valve is in the full circuit orientation and there is no signal from the sensor to the controller. As the rotating member continues to turn, the valve eventually enters the short circuit orientation, as shown in FIG. 12, wherein the flow of heat exchange fluid is cut off from the catheter. At this position, contact 224 is not yet in contact with electrical contact pad 228, thus a signal has not yet been sent from the temperature sensor 80 to the controller, allowing the necessary short circuit period (e.g. 15 seconds) of non-flow within the heat exchange catheter to allow the temperature of the fluid within the heat exchanger to equilibrate with the blood so that the temperature sensed by sensor 80 is an accurate representation of the blood temperature.

The exchange fluid flow continues to cause the flow valve to rotate until contact is made between contact 224 and electrical contact pad 228 and a temperature signal is sent from sensor 80 to the controller, as depicted in FIG. 13. Finally, as shown in FIG. 14, the valve continues to rotate, contact between contact 224 and electrical contact pad 228 is broken and the temperature signal from sensor 80 is interrupted and the full circuit flow is resumed.

The controller only receives a temperature signal after the circulation has been diverted away from the heat exchange catheter and the fluid in communication with the catheter allowed to equilibrate. As previously mentioned, a short period, perhaps only 15 seconds, is all that is necessary to allow the temperature sensed to be an accurate representation of the blood temperature. However, the short period may be greater or less, depending on the individual environment. The flow interruption valve is actuated by the flow of the fluid, and the same valve rotation creates the electrical connection between the controller and the sensor, thus no additional mechanical mechanism or electrical signal is needed from the controller. A signal can be reliably obtained periodically. Although it will not be exactly the same time for each catheter, if the flow rate of each catheter varies slightly, none the less it will be sufficiently uniform. It will also vary in the correct direction, that is if the flow is greater and thus the heat exchange with the body faster, the temperature will be sampled more often.

The controller will be programmed to respond appropriately to the temperature signal. For example, it will need to expect a temperature signal within a particular time window, and to continue to run the heat exchange pump in the interim between the temperature signals, and to adjust the heat exchange units to adjust the temperature of the heat exchange fluid appropriately in response the signal it receives. The controller may provide an alarm or an error signal if it does not receive the signal within the appropriate time window, and thus alert the operator to some potential error. It may even be programmed with fuzzy logic so that its expectations of the time window for receiving the signal will become more accurate as the number of temperature samples increases for a given heat exchange catheter/cassette combination.

The timing of the change of orientation of the diverter valve may be controlled according to several schemes. In another embodiment, the diverter valve is activated periodically for a set time, for example, every 15 minutes for 30 seconds. In another alternative embodiment, the valve is activated periodically until the sensed temperature is stable for a certain length of time (for example, one second) which indicates that the sensed temperature accurately represents the core temperature of the patient.

In yet another embodiment, the timing of the activation of the valve may be variable, depending on a desired rate of temperature change, and can be varied in accordance with a number of factors such as, for example, the rate of change of temperature over the last two or three stoppage intervals and the sensed temperature compared to the target temperature. For example, as the sensed temperature approaches the target temperature, the flow of heat exchange fluid may be diverted more frequently to obtain measurements at closely spaced intervals to avoid overshoot or undershoot of the patient's actual core body temperature. Similarly, if the controller may increase the interval between heat exchange fluid diversions if the last two or three temperature measurements are the same within a pre-determined tolerance, suggesting that the patient has stabilized at the desired target temperature.

It will be appreciated by those skilled in the art, that fuzzy logic and interaction between variables may all be programmed into the controller so that it can respond to these temperature inputs as desired. The measured temperatures may be used to create a predictive curve. For example, if the rate of change of sensed temperature indicates that the patient's core temperature will not reach the target temperature for 30 minutes, the controller may continue to cool the patient's blood stream without stoppage, either by stopping the pump or by diverting the flow of heat exchange fluid, uninterrupted for 25 minutes before taking a temperature measurement, rather than stopping the flow of fluid to measure the patient's blood temperature every 5 minutes. Alternatively, a closed loop feedback system may be employed.

One advantage of using a diverter such as described above is that in practice such a system may minimize cooling time lost in cooling the patient to the desired target temperature as a result of stopping of substantially slowing the flow of heat exchange fluid to the catheter. The heater/cooler element continues to cool the heat exchange fluid circulating within the cassette, thus maintaining the cooling power of the heat exchange fluid. As a result, when the flow through the catheter is restored, there will be greater temperature differential between the heat exchange fluid and the patient's blood, providing a short period of greater heat exchange between the blood and the heat exchange fluid. Thus, over the entire treatment time, the total amount of heat exchange will be approximately the same whether the flow of heat exchange fluid is diverted or if the flow is continuous.

As previously described, a temperature sensor 80 may be located approximately 3-10 centimeters, and typically, about 5 centimeters, from the distal tip of heat exchange catheter (FIG. 2). In some embodiments, however, such as where the pump is stopped or the fluid flow is diverted, the sensor 80 may be positioned about 1 centimeter from the distal tip of the catheter, flush with the catheter tip, or anywhere inside of the catheter lumen, on the catheter shaft or inside the catheter shaft.

When placing a temperature sensor near the heat exchanger of an endovascular heat exchange catheter, the heat transfer between the catheter and blood significantly affects the sensor measurements such that the measurements may not track or correlate well with core body temperature. For example, if the temperature management system is circulating 2° C. fluid within the catheter in order to cool the patient, then a temperature gradient will exist between the blood and the catheter. The temperature range within the blood could be very large due to the laminar nature of the blood flow. For example, in the case where there is incomplete or delayed mixing of the blood flowing past the heat exchanger, a layer of blood adjacent to the catheter may be warmer or cooler that a layer of blood further from the catheter.

The thermistors used to measure the temperature of the blood are typically so sensitive and capable of taking measurements so fast that the fluctuations in the temperature of the blood as it flows past the heat exchange catheter result in substantial fluctuation in the signals communicated to the controller by the sensor 80. This signal fluctuation, which can be clearly seen in the graph of FIG. 16 in the line identified by reference numeral 300, affects the accuracy of the determination of the core body temperature. Moreover, the larger the difference between the heat exchange fluid and the blood temperature of the patient, such as is the case at the beginning of the heating or cooling treatment, the greater the fluctuation in the sensed signal. The amplitude, frequency, and average of the fluctuations depend on a variety of factors such as the location of the temperature sensor with respect to the catheter, sensor sensitivity, heat exchange capability of the catheter system, blood flow rate, movement of the sensor within the blood flow and the like.

The inventors have determined that the fluctuation in signals provided by the thermistors of sensor 80 can be analyzed to provide an accurate estimation of the actual core body temperature. One embodiment of the present invention provides a method for filtering out the fluctuating temperature signals in order to select sensed temperatures that are least affected by the cool or warm catheter.

As discussed previously, there tends to be a temperature gradient within the blood flowing over and past the heat exchange catheter such that blood closest to the catheter is either warmer or cooler (depending on whether the blood is being warmed or cooled) than blood flowing further away from the catheter, for example, near the vessel wall. This temperature gradient, which may be thought of, in the simplest sense, as layers of blood having different temperature, is typically still present when the blood flows past the sensors, with complete mixing generally occurring further downstream of the sensor.

In the case of cooling, the warmest temperature signals sensed by the sensors, or highest sensed temperature "peaks", have been found to more closely approximate the temperature of the blood after complete mixing has occurred. Conversely, the coolest temperature signals, or lowest temperature "peaks", more closely approximate the blood temperature after complete mixing has occurred. By analyzing the temperature peak signals, the method of this embodiment is capable of providing temperatures to the control system that more closely approximate the patient's core body temperature, which are then used by the controller to controllably heat, cool or maintain the temperature of the patient's blood.

Figure 16:
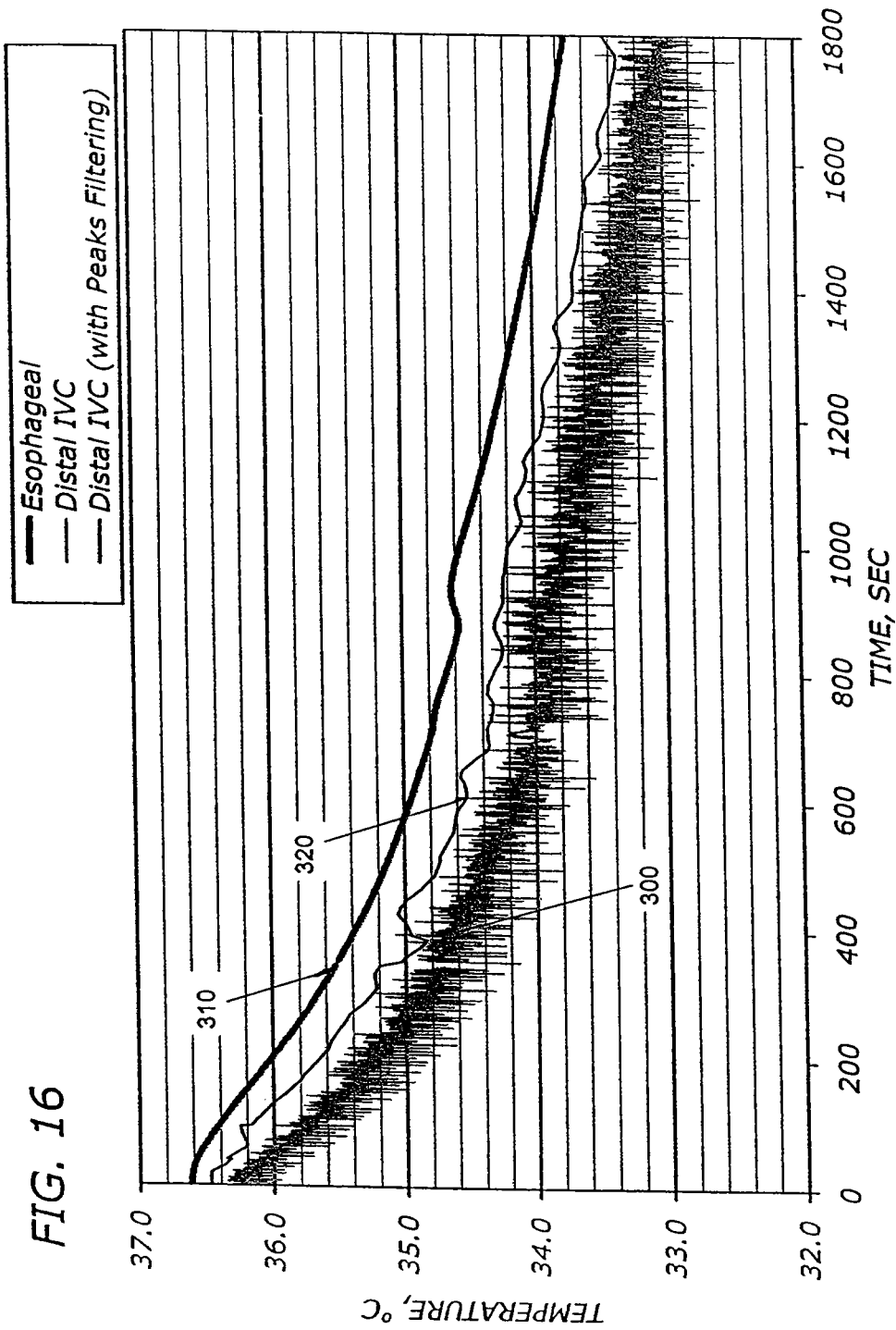
FIG. 16 is a graphical presentation of temperature data accumulated using another embodiment of the present invention to controllably cool and warm a test subject.

As shown in FIG. 16, where line 310 is a graph of body temperature measured using an esophageal temperature probe, considered to be an accepted standard of core body temperature measurements, and line 320 is a graph representing the calculated "peaks" of the fluctuating signal of line 300, line 320 (Peaks) closely tracks the temperature measured using the esophageal temperature recorded in line 310. Alternatively, in the case where the patient's blood is being warmed, the bottom of the peaks of line 300 would approximate the actual temperature of the patient.

The controller may be programmed to analyze the fluctuating temperature signals in a number of ways to determine the peak of the signals. In one embodiment, the controller samples the signals received from the temperature sensor every second. Using a rolling analysis method, the controller determines the highest temperature (during a cooling treatment) that occurred during the previous 10 second interval. This temperature value is stored in a memory associated with or accessible by the controller. The timing interval is incremented by one second, and the controller then determines the highest temperature that was measured during the next 10 second interval, stores that value, increments the timing interval by one second, determines the highest temperature that was measured the next 10 second interval, and stores that value. This process continues in a similar manner for the next interval. After thirty seconds has elapsed, the controller calculates an average of the previous thirty peak values. During the next second, the controller calculates a new average based on the most recent thirty peak values. In this embodiment, the thirty second moving average is used as an input to the temperature controller to determine how the heater/cooler element should be controlled to achieve the desired target temperature.

To further illustrate the previous embodiment, when the pump is first turned on, time T=0, the controller samples the signals communicated to it from the sensor 80 (FIG. 1) at, for example, one second intervals. At T=10, the controller determines the highest temperature value for the first period T=1 to 10, and stores that value. The controller then determines the highest temperature value for the second period T=2 to 11, and stores that value. The controller then determines the highest temperature value for the third period T=3 to 12 and stores that value. At the thirtieth period T=30 to 39, the controller then determines, for example, an average of the thirty values determined for periods 1-30, and uses that value and similarly calculated subsequent values to control the heater/cooler element.

It will be understood that the intervals and periods discussed above are used for description only, and other sample schemes may be used. For example, the highest temperature value may be determined for intervals of 5 seconds, and more or less periods may be analyzed to determine the value used to control heater/cooler element.

Using the above methods, the inventors have determined that the calculated temperature is typically less than approximately 1 degree different, biased in favor of the heat exchange catheter, from the esophageal temperature or temperature measured in the superior vena cava (SVC) of the patient. For example, the calculated temperature is typically 1 degree centigrade less than the SVC temperature during cooling, and 1 degree greater than the SVC temperature during warming of the patient. This accuracy is obtained without the need to stop the flow of heat exchange fluid to the heat exchange catheter.

The method of the above described embodiment has been found to be particularly useful when the difference between the measured temperature, including any fluctuations, and the actual temperature is small, for example, less than 2° C. For example, the accuracy of the calculated temperature using the above described method would not achieve as much improvement if the measured temperature is 5 degrees or more from the blood temperature during maximum rate cooling.

While the above embodiment based on determining the temperature from the peaks of the temperature signal is particularly useful where movement of the catheter is minimized because it provides a real-time estimation of patient temperature, in cases where large temperature gradients between the temperature of the heat exchange catheter and the blood temperature are expected, such as at the start of heating or cooling of the patient, it may be more desirable to utilize the method of interpolating the temperature of the patient by taking temperature measurements when flow of the cooling fluid to the heat exchanger is slowed or stopped, as set forth in the description of another embodiment of the invention described above. It will be understood, and which will be discussed in more detail below, that the two embodiments can be combined, with the controller using one or the other depending on the temperature measurements received or other events that occur, such as changes in the cooling or heating rate, movement of the patient, and the like, to achieve an accurate estimate of the temperature of the patient to use in controlling the heating or cooling process.

The method of the embodiment that analyzes the peaks of the temperature signal is particularly useful when used in conjunction with a temperature sensor located at least 3-7 cm, and preferably 5 or more cm, distal from the catheter tip. In such a case, the measured temperature may fluctuate +/−0.5 degree with the average temperature being 0.5 degree different from the unbiased blood temperature. For example, if the blood temperature is 35.0° C. before it passes over the heat exchanger of a cooling catheter, a probe located 5 cm distal of the catheter tip may measure temperatures in the range of, for example, 33.5 to 34.5° C. The average of these temperature fluctuations may typically be about 34.0 degrees, or approximately 1.0 degree below the unbiased blood temperature. Using the peak determination embodiment of the present invention, the temperature fluctuations would be analyzed to interpolate a temperature of about 34.5° C., or about 0.5° C. below the unbiased blood temperature.

One important advantage of using the embodiment of the method of the present invention that analyzes the peaks of the temperature signals to estimate the core body temperature of the patient is that controlling the heating or cooling of the patient using these calculated temperatures prevents heating or cooling the patient beyond the target temperature. For example, in a patient whose blood is being cooled at the maximum rate to a target temperature of 33.0° C. where the average blood temperature entering the IVC is 34.0° C., the temperature of the heat exchange fluid circulating within the heat exchange catheter is typically 2 to 5° C. After the blood has passed over the heat exchange catheter and begins to mix, the range of blood temperatures past the heat exchange element must be less than or equal to 34.0° C., since the heat exchange element is cooler than the blood and nothing else within the IVC could warm the blood significantly. When the temperature sensor is located 5 to 7 cm distal of the heat exchange element, the measured temperature may be observed to rapidly fluctuate in the range of 32.5 to 33.5 degrees. Using the peaks analysis method of the present invention, the controller filters out the temperature fluctuations and interpolates a blood temperature of 33.5° C., that is, 0.5° C. below the 34.0° C. initial blood temperature. As the interpolated temperature approaches the target temperature, the controller will begin to regulate and warm the fluid circulating within the heat exchanger to prevent the patient's temperature from overshooting, that is, falling below, the target temperature.

In this example, there is a 0.5 degree offset between the interpolated temperature and the actual temperature. If the offset remains fairly constant as the interpolated temperature reaches the 33.0° C. target temperature, the controller would undershoot the target by 0.5 degrees since the actual blood temperature would be 33.5° C.

However, the offset should actually decrease as the controller actively regulates the heat exchange fluid temperature in order to maintain the target temperature. As mentioned above, as the interpolated temperature approaches the target temperature, the controller will begin to warm the heat exchange fluid circulating within the heat exchanger. As the temperature of the heat exchange fluid rises, the temperature difference between the heat exchanger and blood temperature decreases. This results in a decrease in heat transfer between the heat exchange element and blood, further resulting in the distal temperature sensor measuring smaller temperature fluctuations and the existence of a smaller offset between the interpolated patient temperature and actual temperature. Thus, it should be apparent to those skilled in the art that using the peaks analysis embodiment of the present invention prevents overcooling of the patient's blood, an important safety consideration. Similarly, it will also be apparent that in the case where the patient's blood is being warmed, using the peaks analysis embodiment of the present invention will prevent the patient's blood from being overwarmed.

An additional advantage of the peaks analysis embodiment of the present invention is that it provides continuous, real-time temperature feedback to the control system without requiring the flow of the heat exchange fluid to be slowed or stopped to the heat exchanger of the heat exchange catheter.

Thus, using this embodiment, the controller is capable of detecting sudden changes in patient temperature due to, for example, shivering or changes in an external warming apparatus, such as a warming blanket, that falls off the patient or has its temperature changed. Moreover, the warming or cooling of the patient may continue without interruption in therapy, thus resulting in little or no additional time for the patient's temperature to reach the target temperature, as is typically required by prior art methods of slowing or halting flow of the heat exchange fluid to the heat exchanger. Further, this embodiment allows useful temperatures to be obtained using temperature sensor located near, or slightly distal of the heat exchanger, a sensor location previously thought to be disadvantageous because of the temperature fluctuations measured by sensors disposed at such locations.

In a further embodiment of the present invention, the methods described above for stopping the flow of heat exchange fluid to the heat exchange catheter and for determining the peaks of the noise in the temperature signal may be combined to further improve the accuracy of measurement of the patient's temperature during heating or cooling, and to thus further improve the control of the heating or cooling procedure to prevent under or over shoot. These methods also aid in maintaining the target temperature of the patient once the target temperature is reached.

For example, in one embodiment of the present invention, the method of determining the peaks of the signals received from the sensor may be used to control the heating or cooling of the patient. The pump may be stopped, or the heat exchange fluid diverted, at pre-determined intervals, and the difference between the calculated temperature obtained during the stoppage compared to the peak temperature to determine an offset representative of the sensed temperature and the temperature of the blood in the patient's inferior vena cava (IVC). Alternatively, the circulation of heat exchange fluid to the heat exchanger may be stopped according to other factors, such as rate of temperature change, the difference between measured temperature and target temperature, a change in the temperature of the heat exchange fluid, pump motor speed or other events observed by the controller.

For example, in another embodiment, the flow of heat exchange fluid to the heat exchange catheter may be stopped when, for example only, and not limited to, the operator changes the target temperature, the cooling or heating rate or changes the maximum, minimum or range of the temperature of the heat exchange fluid. Alternatively or additionally, the controller may monitor the calculated peak temperature, and command the stoppage of heat exchange fluid circulation when the controller detects a sudden change in patient temperature, such as when the patient shivers, or when a supplemental warming device, such as a warming blanket, falls off the patient or is otherwise displaced. When such events occur, the controller is thus capable of determining, or re-determining, the offset between the sensed temperature during interruption of flow and the IVC (or other standard) temperature, and modify the control of the heater/cooler element or fluid flow to the heat exchange catheter accordingly.

Alternatively, rather than calculating a static offset that is adjusted only infrequently, if at all, during the cooling or warming period, the offset may be dynamically determined based on various factors, such as, for example, sensed temperature and heat exchange fluid temperature. The dynamic offset may be calculated using linear, logarithmic or exponential models. For example, in one embodiment of the present invention, the dynamic offset may be calculated using the equation:

$$Offset_{RT} = \frac{Offset_{Calc} \cdot \ln|\Delta PF_{RT}|}{\ln|\Delta PF_{Calc}|}$$

where:
$Offset_{RT}$=Dynamic real time offset
$Offset_{Calc}$=Offset calculated when flow stopped; calculated as:

$$Offset_{Calc} = T_{Core} - T_{Peak}$$

where:
$T_{Core}$=Temperature sensed after flow is stopped for a selected period and sensed temperature equilibrium is reached
$T_{Peak}$=Temperature sensed just before flow is stopped
$\Delta PF_{RT}$=Real time temperature differential between an instantaneous peak sensed blood temperature and the corresponding instantaneous temperature measurement of the heat exchange fluid.
$\Delta PF_{Calc}$=Temperature differential between the peak blood temperature sensed just before flow stoppage and the corresponding temperature of the heat exchange fluid measured at the same time.

As can be seen from the above equation, the logarithmic model used to calculate the dynamic offset will dynamically correct the filtered sensed temperature estimate such that the filtered temperature approximates the actual temperature of the blood after it has been well mixed after passing by the heat exchange catheter. Using this method, one skilled in the art will understand that as the temperature of the heat exchange fluid approaches the sensed temperature, the offset will decrease. This method is particularly useful in a situation where events, such as changes in cooling rate, heat exchange fluid temperature, or the placing or removal of an external heating blanket occur that necessitate adjustments to the offset. It will also be understood that when cooling the patient, that is, when the temperature of the heat exchange fluid is less than the temperature of the patient, the absolute value of the offset is added to the filtered temperature. Similarly, where warming of the patient is desired, that is, when the temperature of the heat exchange fluid is greater than the temperature of the patient, the absolute value of the offset is subtracted from the filtered temperature.

While particular embodiments of the invention have been described above, for purposes of or illustration, it will be evident to those skilled in the art that numerous variations of the above described embodiments may be made without departing from the invention as defined in the appended claims.

We claim:

1. A heat transfer catheter system, comprising:
a heat transfer catheter insertable into a patient;
a heat exchange unit having a fluid pathway therewithin and incorporating an integral pump head adapted to move fluid through the fluid pathway;
conduits coupled to the heat transfer catheter and heat exchange unit that enable circulation of a heat exchange medium therebetween upon operation of the pump head;
a diverter unit that periodically redirects the fluid pathway, bypassing the heat transfer catheter; and
a master control unit having a heater/cooler and a pump driver, the heat exchange unit being adapted to couple to the master control unit such that the pump driver engages the integral pump head and so that the fluid pathway is in thermal communication with the heater/cooler, the master control unit controlling the diverter unit to periodically interrupt fluid circulation within the heat exchange unit and the heat transfer catheter, the master control unit configured
to receive a target temperature input from an input device and a sensor signal from a temperature sensor,
to analyze the signal from the sensor during the fluid flow interruption to determine a rate of change of the temperature as a function of time,
to compare the determined temperature to a target temperature,
to restart the flow of heat exchange medium through the heat transfer catheter, and
to control the rate at which the patient temperature approaches the target temperature by controlling the heater/cooler to add or remove thermal energy from the heat exchange medium.

2. The system of claim 1, wherein the diverter unit is a diverter valve activated by the controller.

3. The system of claim 1, wherein the diverter unit is a flow actuated valve.

4. The system of claim 1, wherein the master control unit defines a cavity into which the heat exchange unit couples.

5. The system of claim 1, wherein the heater/cooler comprises a thermoelectric heater/cooler.

6. The system of claim 1, further including a plurality of sensors supplying patient data to the master control unit, the master control unit being adapted to operate the heater/cooler based on the supplied patient data.

7. The controller of claim 1 wherein the master control unit comprises a microprocessor responsive to each of the sensors to control the heater/cooler.

8. A system for regulating the temperature of at least a portion of a patient's body, comprising:
a heat remover;
a heat exchange catheter for insertion into a lumen of the patient's body, the heat exchange catheter having conduits that enable circulation of a heat exchange medium between a heat exchange portion of the catheter and the heat remover for removing thermal energy from the heat exchange medium;
a temperature sensor disposed in the lumen downstream of the heat exchange catheter for providing temperature signals representative of the temperature of body fluid flowing through the lumen; and
a controller including a processor and a memory, the processor capable of being programmed by software to
sample the temperature signals at a selected interval,
determine a peak temperature value occurring during the selected interval and store that determined value in a memory of the controller,
increment the selected range of selected intervals a selected number of times and, after each increment, repeating determining the peak temperature value sampled within the incremented selected range of selected intervals and storing that value, and
calculate a dynamic offset value as follows:

$$Offset_{RT} = \frac{Offset_{Calc} \cdot \ln|\Delta PF_{RT}|}{\ln|\Delta PF_{Calc}|}$$

where:
$Offset_{RT}$=Dynamic real time offset
$Offset_{Calc}$=Offset calculated when flow stopped; calculated as:

$$Offset_{Calc} = T_{Core} - T_{Peak}$$

where:
- $T_{Core}$=Temperature sensed after flow is stopped for a selected period and sensed temperature equilibrium is reached
- $T_{Peak}$=Temperature sensed just before flow is stopped
- $\Delta PF_{RT}$=Real time temperature differential between an instantaneous peak sensed blood temperature and the corresponding instantaneous temperature measurement of the heat exchange fluid
- $\Delta PF_{Calc}$=Temperature differential between the peak blood temperature sensed just before flow stoppage and the corresponding temperature of the heat exchange fluid measured at the same time, add the offset value to the peak temperature before comparing the peak temperature to the target temperature, the controller responsive to the comparison to control the heater/cooler to add or remove thermal energy from the heat exchange medium.

9. The system of claim 8, wherein the temperature sensor is configured to move within the lumen in response to the flow of body fluid within the lumen.

* * * * *